US012779069B2

(12) United States Patent
Mao et al.

(10) Patent No.: US 12,779,069 B2
(45) Date of Patent: Nov. 3, 2026

(54) COMPOSITIONS AND METHODS FOR REDUCING BIOBURDEN IN CHROMATOGRAPHY

(71) Applicant: Regeneron Pharmaceuticals, Inc., Tarrytown, NY (US)

(72) Inventors: Nathan L. Mao, Cohoes, NY (US); Wenbin Qi, Carlsbad, CA (US); Bernhard Schilling, Hudson, NY (US); Scott Carver, Wynantskill, NY (US)

(73) Assignee: Regeneron Pharmaceuticals, Inc.

( * ) Notice: Subject to any disclaimer, the term of this patent is extended or adjusted under 35 U.S.C. 154(b) by 583 days.

(21) Appl. No.: 18/218,532

(22) Filed: Jul. 5, 2023

(65) Prior Publication Data

US 2023/0343086 A1 Oct. 26, 2023

Related U.S. Application Data

(60) Division of application No. 17/848,936, filed on Jun. 24, 2022, now Pat. No. 11,717,586, which is a (Continued)

(51) Int. Cl.
*A61L 2/08* (2026.01)
*A61L 2/18* (2006.01)
(Continued)

(52) U.S. Cl.
CPC .................. *A61L 2/18* (2013.01); *A61L 2/28* (2013.01); *B01D 15/20* (2013.01); *B01D 15/3809* (2013.01); *G01N 30/50* (2013.01); *G06V 20/10* (2022.01); *G06V 20/46* (2022.01); *G08G 1/0175* (2013.01); *G01N 2030/8831* (2013.01); *G06V 20/625* (2022.01); *G06V 2201/08* (2022.01)

(58) Field of Classification Search
CPC ........ A61L 2/0017; A61L 2/0088; A61L 2/18; A61L 2202/20; A61L 2202/21; C12N 11/00; B01D 15/08; B01D 65/02
USPC ...... 422/28, 30; 435/174; 210/635, 656, 679
See application file for complete search history.

(56) References Cited

U.S. PATENT DOCUMENTS

| | | | | |
|---|---|---|---|---|
| 4,919,837 A * | 4/1990 | Gluck | A01N 47/44 510/132 | |
| 5,202,246 A | 4/1993 | Kruse et al. | | |

(Continued)

FOREIGN PATENT DOCUMENTS

| | | |
|---|---|---|
| EP | 3141558 A1 | 3/2017 |
| JP | 2010518376 A | 5/2010 |

(Continued)

OTHER PUBLICATIONS

Allen, et al. Antibody variable region Interactions with Protein A: implications for the development of generic purification processes// Biotechnol Bioeng . Dec. 20, 2005;92(6):665-73.

(Continued)

*Primary Examiner* — Monzer R Chorbaji
(74) *Attorney, Agent, or Firm* — Troutman Pepper Locke LLP

(57) ABSTRACT

The invention provides methods for microbial bioburden reduction of various chromatography matrices, including bioburden reduction in the context of large-scale Protein A-based affinity chromatography columns.

20 Claims, 19 Drawing Sheets

Related U.S. Application Data continuation of application No. 17/153,205, filed on Jan. 20, 2021, now Pat. No. 11,369,707, which is a division of application No. 15/882,845, filed on Jan. 29, 2018, now Pat. No. 10,925,986.

(60) Provisional application No. 62/452,140, filed on Jan. 30, 2017.

(51) Int. Cl.

| | |
|---|---|
| ***A61L 2/28*** | (2006.01) |
| ***A61L 9/00*** | (2006.01) |
| ***B01D 15/08*** | (2006.01) |
| ***B01D 15/20*** | (2006.01) |
| ***B01D 15/38*** | (2006.01) |
| ***C12N 11/00*** | (2006.01) |
| ***G01N 30/50*** | (2006.01) |
| ***G06V 20/10*** | (2022.01) |
| ***G06V 20/40*** | (2022.01) |
| ***G08G 1/017*** | (2006.01) |
| *G01N 30/88* | (2006.01) |
| *G06V 20/62* | (2022.01) |

(56) References Cited

U.S. PATENT DOCUMENTS

| | | | | |
|---|---|---|---|---|
| 5,521,073 | A | 5/1996 | Davis et al. | |
| 5,650,496 | A | 7/1997 | Brierley et al. | |
| 5,676,837 | A | 10/1997 | Jungbauer et al. | |
| 6,022,694 | A | 2/2000 | Radzlejewski et al. | |
| 6,166,185 | A | 12/2000 | Davis et al. | |
| 6,913,695 | B2 | 7/2005 | Jones et al. | |
| 7,320,784 | B1 | 1/2008 | Pollack et al. | |
| 7,867,784 | B2 | 1/2011 | Engstrand et al. | |
| 8,343,912 | B2 * | 1/2013 | Leese | C07K 7/62 530/319 |
| 2004/0019197 | A1 | 1/2004 | Norman et al. | |
| 2005/0006307 | A1 * | 1/2005 | Jones | A61L 2/18 210/764 |
| 2009/0095668 | A1 | 4/2009 | Busson | |
| 2010/0112597 | A1 | 5/2010 | Bian | |
| 2012/0264920 | A1 | 10/2012 | Wang et al. | |
| 2012/0282654 | A1 | 11/2012 | Yao et al. | |
| 2013/0280788 | A1 | 10/2013 | Skudas | |
| 2014/0154270 | A1 | 6/2014 | Wang et al. | |
| 2015/0093800 | A1 | 4/2015 | Mahajan et al. | |

FOREIGN PATENT DOCUMENTS

| | | | |
|---|---|---|---|
| WO | 200127623 | A2 | 4/2001 |
| WO | 2005007204 | A1 | 1/2005 |
| WO | 2006033634 | A1 | 3/2006 |
| WO | 2011050071 | A2 | 4/2011 |
| WO | 2015034566 | A1 | 3/2015 |
| WO | 2015354180 | A1 | 3/2015 |
| WO | 2016056453 | A1 | 4/2016 |
| WO | 2016139128 | A1 | 9/2016 |
| WO | 2016149088 | A1 | 9/2016 |

OTHER PUBLICATIONS

Carter, H. el al., "Testing a New Chromatography Column for Cleaning Effectiveness", BioPharm International (2006), vol. 19, Issue 1, 6 pages.

Communications (International Preliminary Report of Patentability) issued by the International Searching Authority in International Application No. PCT/US2018/015764 dated Jun. 30, 2019, 11 pages total.

Communications (International Search Report and Written Opinion) issued by the International Searching Authority in International Application No. PCT/US2018/015764 dated Jun. 28, 2018, 19 pages total.

EPO Communication pursuant to Article 94(3) EPC issued Sep. 27, 2022 for EP Application No. 18706335.9 (5 pages).

GE Healthcare Life Sciences, "Instructions 11-0026-02 AW Mabselect XTRA" (2011) 28 pages total.

GE Healthcare Life Sciences, "Instructions 28-9765-00 AA MabSelect SuRe LX" (2011) 28 pages total.

GE Healthcare Life Sciences, "Instructions 71502091AF MabSelect" (2006) 28 pages total.

GE Healthcare Life Sciences, "Three Step Monoclonal antibody purification Processes using Modern Chromatography Media" (2015) 8 pages total.

Israeli Communication (Official Action) issued by the Israel Patent Office in Israel Patent Application No. 287543 dated May 1, 2022 (4 pages of English translation).

Mahajan, E. et al., "One Resin, Multiple Products: A Green Approach to Purification" American Chemical Society (2013) 25 pages total.

Merck, "Data Sheet: ProSep Ultra Plus Chromatography Media" (2014) 8 pages total.

Merck, "Technical Brief: PAB—An Enhanced Sanitization Option for ProSep Protein A Affinity Chromatography Media" (2014) 4 pages total.

MoBiTec, Molecular Biotechnology "Protein A Columns" MoBiTec GmbH (2015).

Pena-Fornes, W., "Challenges Around Process Validation During Tech Transfers", AMGEN (Aug. 1, 2016).

Rogers, M. et al., "Development of a Rapid Sanitization Solution for Silica-Based Protein A Affinity Adsorbents" Journal of Chromatography A (2009) vol. 1216, No. 21, pp. 4589-4596.

Singapore Communication (Written Opinion) issued by the Intellectual Property Office of Singapore in Singapore Application No. 11201905510X dated Apr. 21, 2020, 7 pages total.

Singapore Communication (Written Opinion) issued by the Intellectual Property Office of Singapore in Singapore Application No. 11201905510X dated Sep. 3, 2020, 5 pages total.

* cited by examiner

Oneway Anova

Analysis of Variance

| Source | DF | Sum of Squares | Mean Square | F Ratio | Prob > F |
|---|---|---|---|---|---|
| Conditio | 1 | 0 | 0 | . | . |
| Error | 4 | 0 | 0 | | |
| C. Total | 5 | 0 | | | |

Oneway Anova

Analysis of Variance

| Source | DF | Sum of Squares | Mean Square | F Ratio | Prob > F |
|---|---|---|---|---|---|
| Conditio | 1 | 0.04681667 | 0.046817 | 3.7058 | 0.1265 |
| Error | 4 | 0.05053333 | 0.012633 | | |
| C. Total | 5 | 0.09735000 | | | |

Oneway Analysis of Non-Reduced Percent Purity (%) By Condition

Oneway Anova

Analysis of Variance

| Source | DF | Sum of Squares | Mean Square | F Ratio | Prob > F |
|---|---|---|---|---|---|
| Conditio | 1 | 0.04335000 | 0.043350 | 0.6656 | 0.4604 |
| Error | 4 | 0.26053333 | 0.065133 | | |
| C. Total | 5 | 0.30388333 | | | |

Oneway Analysis of Protein A (ppm) By Condition

Oneway Anova

Analysis of Variance

| Source | DF | Sum of Squares | Mean Square | F Ratio | Prob > F |
|---|---|---|---|---|---|
| Conditio | 1 | 0.7920667 | 0.792067 | 3.4136 | 0.1384 |
| Error | 4 | 0.9281333 | 0.232033 | | |
| C. Total | 5 | 1.7202000 | | | |

Oneway Analysis of iCIEF Region 2 (%) By Condition

Oneway Anova

Analysis of Variance

| Source | DF | Sum of Squares | Mean Square | F Ratio | Prob > F |
|---|---|---|---|---|---|
| Conditio | 1 | 0.0266667 | 0.026667 | 0.0319 | 0.8670 |
| Error | 4 | 3.3466667 | 0.836667 | | |
| C. Total | 5 | 3.3733333 | | | |

Oneway Analysis of SE HPLC Purity (%) By Condition

Oneway Anova

Analysis of Variance

| Source | DF | Sum of Squares | Mean Square | F Ratio | Prob > F |
|---|---|---|---|---|---|
| Conditio | 1 | 2.2693500 | 2.26935 | 26.7349 | 0.0066* |
| Error | 4 | 0.3395333 | 0.08488 | | |
| C. Total | 5 | 2.6088833 | | | |

Oneway Analysis of Reduced Total LC + HC Percent Purity (%) By Condition

Oneway Anova

Analysis of Variance

| Source | DF | Sum of Squares | Mean Square | F Ratio | Prob > F |
|---|---|---|---|---|---|
| Conditio | 1 | 0.6666667 | 0.666667 | 1.0959 | 0.3543 |
| Error | 4 | 2.4333333 | 0.608333 | | |
| C. Total | 5 | 3.1000000 | | | |

Oneway Analysis of Non-Reduced Percent Purity (%) By Condition

Oneway Anova

Analysis of Variance

| Source | DF | Sum of Squares | Mean Square | F Ratio | Prob > F |
|---|---|---|---|---|---|
| Conditio | 1 | 0.13500000 | 0.135000 | 1.1408 | 0.3456 |
| Error | 4 | 0.47333333 | 0.118333 | | |
| C. Total | 5 | 0.60833333 | | | |

Oneway Analysis of Protein A (ppm) By Condition

Oneway Anova

Analysis of Variance

| Source | DF | Sum of Squares | Mean Square | F Ratio | Prob > F |
|---|---|---|---|---|---|
| Conditio | 1 | 96.80167 | 96.8017 | 1.0056 | 0.3727 |
| Error | 4 | 385.06667 | 96.2667 | | |
| C. Total | 5 | 481.86833 | | | |

Oneway Analysis of iCIEF Region 2 (%) By Condition

Oneway Anova

Analysis of Variance

| Source | DF | Sum of Squares | Mean Square | F Ratio | Prob > F |
|---|---|---|---|---|---|
| Conditio | 1 | 0.8066667 | 0.806667 | 5.5000 | 0.0789 |
| Error | 4 | 0.5866667 | 0.146667 | | |
| C. Total | 5 | 1.3933333 | | | |

COMPOSITIONS AND METHODS FOR REDUCING BIOBURDEN IN CHROMATOGRAPHY

CROSS REFERENCE TO RELATED APPLICATIONS

This application is a Divisional of U.S. application Ser. No. 17/848,936, filed on Jun. 24, 2022, which is a continuation of U.S. application Ser. No. 17/153,205, filed on Jan. 20, 2021, issued as U.S. Pat. No. 11,369,707, which is a Divisional of U.S. application Ser. No. 15/882,845, filed on Jan. 29, 2018, issued as U.S. Pat. No. 10,925,986, which claims the benefits of U.S. Provisional Patent Application No. 62/452,140, filed on Jan. 30, 2017, all of which applications are incorporated herein by reference in their entireties.

FIELD OF THE INVENTION

The present invention provides methods for microbial bioburden reduction of various chromatography matrices, including bioburden reduction in the context of large-scale Protein A-based affinity chromatography columns.

BACKGROUND OF THE INVENTION

Antibody drugs are the most prevalent biopharmaceutical products. Affinity chromatography, e.g., performed with a natural or engineered staphylococcal protein A ligand, is widely used as a capture method in the antibody drug manufacturing process to remove impurities and contaminants. Protein A binds the Fc-region of antibodies, with protein A columns considered to be selective for purification of monoclonal antibodies. Affinity chromatography with protein A typically involves a clean-in-place (CIP) step to clean and remove impurities that are bound to the column, such as precipitated or denatured substances. CIP is normally performed with a sodium hydroxide solution.

In addition to cleaning, sodium hydroxide solutions, or phosphoric acid solutions with benzyl alcohol, are used to reduce the number of microbes in a protein A chromatography matrix or column. Bacteria from the media used to culture monoclonal-antibody producing cells, as well as associated host cell proteins and DNA, can quickly increase the bioburden of a protein A column during use. The bioburden increases as such bacteria and microbes accumulate on the column. Column performance generally degrades as bioburden increases. Signs of such degradation include decrease in product purity, column packing deterioration, and increased backpressure.

Managing and reducing microbial bioburden on protein A columns is important because protein A columns are very expensive, with the packing and unpacking of such affinity columns being labor intensive. To avoid expenses in replacing the protein A column or adding process steps upstream of protein A column purification, there is a need to find agents that remove a significant amount of bioburden from the column quickly without negatively affecting the structure and function of protein A, and that have few downstream effects.

The importance of microbial bioburden reduction is not limited to protein A chromatography matrices but encompasses other chromatography matrices with proteinaceous ligands coupled to a support as well as matrices not involving proteinaceous ligands such as, e.g., various ion exchange chromatography matrices, hydrophobic interaction chromatography (HIC) matrices, mixed mode chromatography matrices, size exclusion chromatography matrices, etc.

Microbial bioburden reduction of chromatography matrices is particularly important in the context of a good manufacturing practice (GMP), or current good manufacturing practice (CGMP). Such practices must provide consistency in manufacturing steps and quality of product so as to meet requirements of regulatory bodies, such as the U.S. Food and Drug Administration. GMP and CGMP require a high degree of predictability and standardization in manufacturing processes, particularly with ensuring purity of the manufactured therapeutic biomolecules used in human patients. With the labor involved in growing cultures to produce biomolecules, great expense arises when a failure occurs. An excessive bioburden can decrease column performance, which can interfere with purifying the product in a standardized and predictable way and possibly cause other failure points to be triggered.

The agents presently known in the art to reduce bioburden have negative downstream effects. For example, solutions based on sodium hydroxide, and those based on phosphoric acid with benzyl alcohol, may be effective to kill microorganisms but also tend to denature the proteinaceious ligands (e.g., protein A) thus negatively affecting their function.

Further, oxidants and other components of such solutions can remain with the purified monoclonal antibodies and further degrade them downstream.

Thus, those of ordinary skill in the art appreciate that it is difficult to reduce bioburden in chromatography matrices, especially in matrices with proteinaceous ligands, such as protein A chromatography matrices.

SUMMARY OF THE INVENTION

As specified above, there is a need for new effective methods that can be used in the context of large-scale GMP and CGMP to reduce microbial bioburden of various chromatography matrices, and especially those involving proteinaceous ligands such as protein A. The present invention addresses this and other needs by providing compositions and methods for microbial bioburden reduction of chromatography matrices.

In one aspect, the present invention provides a method for microbial bioburden reduction of a chromatography matrix, comprising contacting the chromatography matrix with a composition comprising from about 0.1 M to about 0.5 M acetic acid, wherein the contacting step is performed for at least about 2 hours.

In a related aspect, the invention provides a method for microbial bioburden reduction of a chromatography matrix, comprising contacting the chromatography matrix with a composition comprising from about 0.5 M to about 1.0 M acetic acid, wherein the contacting step is performed for at least about 1 hour.

In a related aspect, the invention provides a method for microbial bioburden reduction of a chromatography matrix, comprising contacting the chromatography matrix with a composition comprising from about 0.1 M to about 1.0 M acetic acid, wherein the contacting step results in one or more of a reduction in the amount of spore forming bacteria by at least 3 $\log_{10}$, a reduction in the amount of gram positive bacteria by at least 5 $\log_{10}$, and a reduction in the amount of gram negative bacteria by at least 5 $\log_{10}$ in the chromatography matrix.

In a separate aspect, the present invention provides a method for microbial bioburden reduction of a chromatography matrix, comprising contacting the chromatography matrix with a composition comprising from about 4.0 M to about 12.0 M urea, wherein the contacting step is performed for at least about 30 minutes.

In a related aspect, the invention provides a method for microbial bioburden reduction of a chromatography matrix, comprising contacting the chromatography matrix with a composition comprising from about 4.0 M to about 12.0 M urea, wherein the contacting step results in one or more of a reduction in the amount of spore forming bacteria by at least 2 $\log_{10}$, a reduction in the amount of gram positive bacteria by at least 5 $\log_{10}$, and a reduction in the amount of gram negative bacteria by at least 5 $\log_{10}$, in the chromatography matrix.

In one embodiment, the invention provides a method for microbial bioburden reduction of MabSelect™ Xtra chromatography matrix, comprising contacting the chromatography matrix with a composition consisting essentially of about 0.5 M acetic acid, wherein the contacting step is performed for at least about 4 hours.

In another embodiment, the invention provides a method for microbial bioburden reduction of MabSelect™ Xtra chromatography matrix, comprising contacting the chromatography matrix with a composition consisting essentially of about 0.1 M acetic acid and about 20% ethanol, wherein the contacting step is performed for at least about 4 hours.

In a further embodiment, the invention provides a method for microbial bioburden reduction of MabSelect™ Xtra chromatography matrix, comprising contacting the chromatography matrix with a composition consisting essentially of about 8 M urea, wherein the contacting step is performed for at least about 1 hour.

In yet another embodiment, the invention provides a method for microbial bioburden reduction of MabSelect™ Xtra chromatography matrix, comprising contacting the chromatography matrix with a composition consisting essentially of about 8 M urea and about 20% ethanol, wherein the contacting step is performed for at least about 1 hour.

In one embodiment, the invention provides a method for reducing microbial load before applying a composition comprising a pharmaceutical agent for purification comprising (a) providing a chromatography matrix; (b) performing any of the above methods of the invention; and (c) applying the composition comprising the pharmaceutical agent to the chromatography matrix.

These and other aspects of the present invention will be apparent to those of ordinary skill in the art in the following description, claims and drawings.

BRIEF DESCRIPTION OF THE DRAWINGS

In FIG. 15, the range is greater after exposure to acid to a statistically significant degree. In FIGS. 16-19, the ranges for pre-acid overlap with those for post-acid. The ANOVA analysis shows no statistically significant negative effect on protein quality from prolonged exposure of the resin to 0.5 M acetic acid.

DETAILED DESCRIPTION

Figure 1:
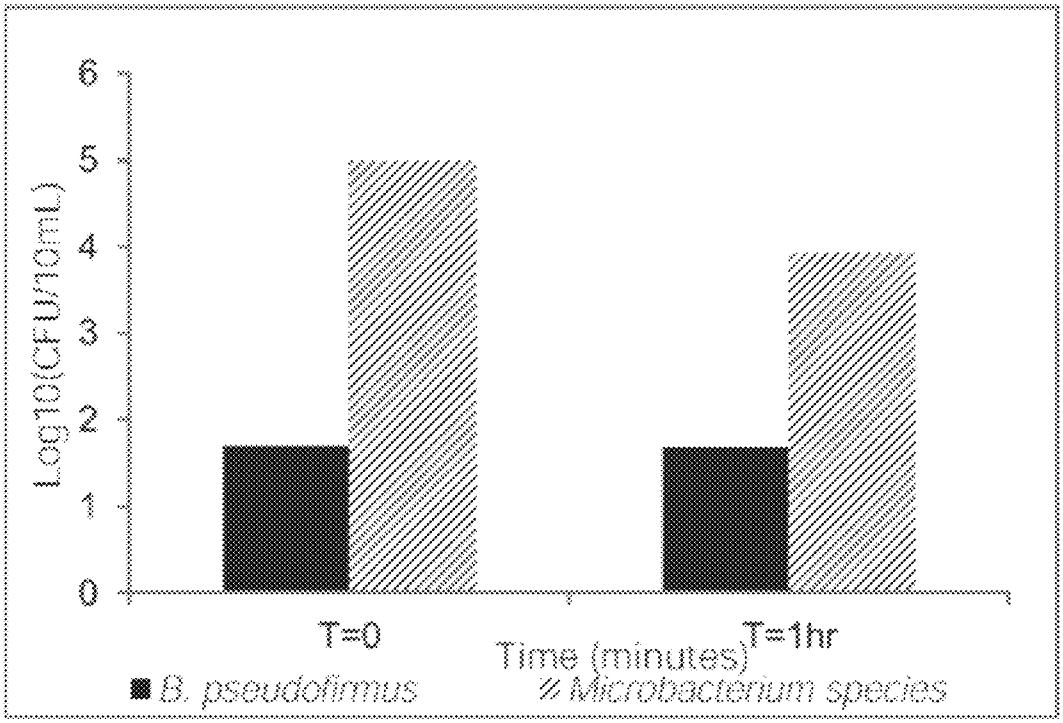
FIG. 1 illustrates the results of a spike study in solution with 0.5 M acetic acid. The extent of bacterial killing is measured in solution, without chromatography matrix present. The black bars represent the amount of *Bacillus psuedofirmus* and the diagonally striped bars represent the amount of *Microbacterium* species in a MabSelect™ Xtra column before exposure with 0.5 acetic acid (T=0) and one hour (T=1 hr) after exposure with acetic acid.

In one aspect, the present invention provides a method for microbial bioburden reduction of a chromatography matrix, comprising contacting the chromatography matrix with a composition comprising from about 0.1 M to about 0.5 M acetic acid, wherein the contacting step is performed for at least about 2 hours. In various embodiments, the contacting step is performed for 2 to 5 hours, 2 to 10 hours, 2 to 25 hours, 2 to 200 hours, 2 to 375 hours, or 2 to 400 hours. In one embodiment, the contacting step is performed for at least about 4 hours. In various embodiments, the contacting step is performed for 4 to 5 hours, 4 to 10 hours, 4 to 25 hours, 4 to 200 hours, 4 to 375 hours, or 4 to 400 hours. In one embodiment, the composition comprises about 0.1 M acetic acid and the contacting step is performed for at least about 4 hours. In one embodiment, the composition comprises about 0.5 M acetic acid and the contacting step is performed for at least about 4 hours. In various embodiments, the composition comprises about 0.5 M acetic acid and the contacting step is performed for 4 to 5 hours, 4 to 10 hours, 4 to 25 hours, 4 to 200 hours, 4 to 375 hours, or 4 to 400 hours.

In one embodiment, the composition further comprises an alcohol. Non-limiting examples of alcohols that can be used include ethanol (e.g., about 20%) and benzyl alcohol (e.g., from about 1% to about 2%). In one specific embodiment, the composition consists essentially of about 0.1M acetic acid and about 20% ethanol.

In one embodiment, the invention provides a method for microbial bioburden reduction of a chromatography matrix, comprising contacting the chromatography matrix with a composition consisting essentially of about 0.1 M to about 0.5 M acetic acid, wherein the contacting step is performed for at least about 2 hours. In one specific embodiment, the contacting step is performed for at least about 4 hours. In various embodiments, the contacting step is performed for 4 to 5 hours, 4 to 10 hours, 4 to 25 hours, 4 to 200 hours, 4 to 375 hours, or 4 to 400 hours. In one specific embodiment, the composition consists essentially of about 0.1 M acetic acid and the contacting step is performed for at least about 4 hours. In another specific embodiment, the composition consists essentially of about 0.5 M acetic acid and the contacting step is performed for at least about 4 hours. In various embodiments, the composition comprises about 0.5 M acetic acid and the contacting step is performed for 4 to 5 hours, 4 to 10 hours, 4 to 25 hours, 4 to 200 hours, 4 to 375 hours, or 4 to 400 hours.

In a related aspect, the invention provides a method for microbial bioburden reduction of a chromatography matrix, comprising contacting the chromatography matrix with a composition comprising from about 0.5 M to about 1.0 M acetic acid, wherein the contacting step is performed for at least about 1 hour. In various embodiments, the contacting step is performed for 1 to 5 hours, 1 to 10 hours, 1 to 25 hours, 1 to 200 hours, 1 to 375 hours, 1 to 400 hours, 4 to 5 hours, 4 to 10 hours, 4 to 25 hours, 4 to 200 hours, 4 to 375 hours, or 4 to 400 hours. In one embodiment, the composition comprises about 0.5 M acetic acid and the contacting step is performed for at least about 1 hour. In various embodiments, the composition comprises about 0.5 M acetic acid and the contacting step is performed for 1 to 5 hours, 1 to 10 hours, 1 to 25 hours, 1 to 200 hours, 1 to 375 hours, 1 to 400 hours, 4 to 5 hours, 4 to 10 hours, 4 to 25 hours, 4 to 200 hours, 4 to 375 hours, or 4 to 400 hours.

In one embodiment, the composition further comprises an alcohol. Non-limiting examples of alcohols that can be used include ethanol (e.g., about 20%) and benzyl alcohol (e.g., from about 1% to about 2%). In one specific embodiment, the composition consists essentially of about 0.5 M acetic acid and about 20% ethanol.

In one embodiment, the invention provides a method for microbial bioburden reduction of a chromatography matrix, comprising contacting the chromatography matrix with a composition consisting essentially of about 0.5 M to about 1.0 M acetic acid, wherein the contacting step is performed for at least about 1 hour. In various embodiments, the composition consists essentially of about 0.5 M to about 1.0 M acetic acid and the contacting step is performed for 1 to 5 hours, 1 to 10 hours, 1 to 25 hours, 1 to 200 hours, 1 to 375 hours, 1 to 400 hours, 4 to 5 hours, 4 to 10 hours, 4 to 25 hours, 4 to 200 hours, 4 to 375 hours, or 4 to 400 hours. In one specific embodiment, the composition consists essentially of about 0.5 M acetic acid and the contacting step is performed for at least about 1 hour. In various embodiments, the composition consists essentially of about 0.5 M acetic acid and the contacting step is performed for 1 to 5 hours, 1 to 10 hours, 1 to 25 hours, 1 to 200 hours, 1 to 375 hours, 1 to 400 hours, 4 to 5 hours, 4 to 10 hours, 4 to 25 hours, 4 to 200 hours, 4 to 375 hours, or 4 to 400 hours.

In a related aspect, the invention provides a method for microbial bioburden reduction of a chromatography matrix, comprising contacting the chromatography matrix with a composition comprising from about 0.1 M to about 1.0 M acetic acid, wherein the contacting step results in one or more of a reduction in the amount of spore forming bacteria (e.g., *Bacillus pseudofirmus*) by at least 3 $\log_{10}$, a reduction in the amount of gram positive bacteria (e.g., *Microbacterium* spp.) by at least 5 $\log_{10}$, and a reduction in the amount of gram negative bacteria (e.g., *Stenotrophomonas maltophilia*) by at least 5 $\log_{10}$ in the chromatography matrix. In one specific embodiment, the contacting step results in a reduction in the amount of one or more of spore forming bacteria (e.g., *Bacillus pseudofirmus*), gram positive bacteria (e.g., *Microbacterium* spp.), and gram negative bacteria (e.g., *Stenotrophomonas maltophilia*), in the chromatography matrix, to below the limit of detection as determined by an assay, such as, for example, (1) a biofiltration assay, (2) microscopic bacterial staining, (3) IR/FTIR spectroscopy method, (4) a sterility test, or (5) a bacterial identification test. In various embodiments, the contacting step is performed for at least about 1 hour, 1 to 5 hours, 1 to 10 hours, 1 to 25 hours, 1 to 200 hours, 1 to 375 hours, 1 to 400 hours, for at least about 4 hours, for 4 to 5 hours, 4 to 10 hours, 4 to 25 hours, 4 to 200 hours, 4 to 375 hours, or 4 to 400 hours.

In one embodiment, the composition further comprises an alcohol. Non-limiting examples of alcohols that can be used include ethanol (e.g., about 20%) and benzyl alcohol (e.g., from about 1% to about 2%). In one specific embodiment, the composition consists essentially of about 0.1 M acetic acid and about 20% ethanol. In one specific embodiment, the composition consists essentially of about 0.5 M acetic acid and about 20% ethanol.

In one embodiment, the invention provides a method for microbial bioburden reduction of a chromatography matrix, comprising contacting the chromatography matrix with a composition consisting essentially of about 0.1 M to about 1.0 M acetic acid, wherein the contacting step results in one or more of a reduction in the amount of spore forming bacteria (e.g., *Bacillus pseudofirmus*) by at least 3 $\log_{10}$, a reduction in the amount of gram positive bacteria (e.g., *Microbacterium* spp.) by at least 5 $\log_{10}$, and a reduction in the amount of gram negative bacteria (e.g., *Stenotrophomonas maltophilia*) by at least 5 $\log_{10}$, in the chromatography matrix. In one specific embodiment, the contacting step results in a reduction in the amount of one or more of spore forming bacteria (e.g., *Bacillus pseudofirmus*), gram positive bacteria (e.g., *Microbacterium* spp.), and gram negative bacteria (e.g., *Stenotrophomonas maltophilia*), in the chromatography matrix, to below the limit of detection as determined by an assay, such as, for example, (1) a biofiltration assay, (2) microscopic bacterial staining, (3) IR/FTIR spectroscopy method, (4) a sterility test, or (5) a bacterial identification test. In various embodiments, the contacting step is performed for at least about 1 hour, 1 to 5 hours, 1 to 10 hours, 1 to 25 hours, 1 to 200 hours, 1 to 375 hours, 1 to 400 hours, at least about 4 hours, 4 to 5 hours, 4 to 10 hours, 4 to 25 hours, 4 to 200 hours, 4 to 375 hours, or 4 to 400 hours.

In one embodiment of any of the above methods of the invention, the composition further comprises an acetate salt.

In one embodiment of any of the above methods of the invention, the composition has pH between about 2 and about 3.

In a separate aspect, the present invention provides a method for microbial bioburden reduction of a chromatography matrix, comprising contacting the chromatography matrix with a composition comprising from about 4.0 M to about 12.0 M urea, wherein the contacting step is performed for at least about 30 minutes. In one embodiment, the contacting step is performed for at least about 1 hour. In one embodiment, the composition comprises about 8 M urea.

In one embodiment, the composition further comprises an alcohol. Non-limiting examples of alcohols that can be used include ethanol (e.g., about 20%) and benzyl alcohol (e.g., from about 1% to about 2%). In one specific embodiment, the composition consists essentially of about 8 M urea and about 20% ethanol.

In one embodiment, the invention provides a method for microbial bioburden reduction of a chromatography matrix, comprising contacting the chromatography matrix with a composition consisting essentially of about 4.0 M to about 12.0 M urea, wherein the contacting step is performed for at least about 30 minutes. In one specific embodiment, the contacting step is performed for at least about 1 hour. In one specific embodiment, the composition consists essentially of 8 M urea.

In a related aspect, the invention provides a method for microbial bioburden reduction of a chromatography matrix, comprising contacting the chromatography matrix with a composition comprising from about 4.0 M to about 12.0 M urea, wherein the contacting step results in one or more of a reduction in the amount of spore forming bacteria (e.g., *Bacillus pseudofirmus*) by at least 2 $\log_{10}$, a reduction in the amount of gram positive bacteria (e.g., *Microbacterium* spp.) by at least 5 $\log_{10}$, and a reduction in the amount of gram negative bacteria (e.g., *Stenotrophomonas maltophilia*) by at least 5 $\log_{10}$, in the chromatography matrix. In one specific embodiment, the contacting step results in a reduction in the amount of one or more of spore forming bacteria (e.g., *Bacillus pseudofirmus*), gram positive bacteria (e.g., *Microbacterium* spp.), and gram negative bacteria (e.g., *Stenotrophomonas maltophilia*), in the chromatography matrix, to below the limit of detection as determined by an assay, such as, for example, (1) a biofiltration assay, (2) microscopic bacterial staining, (3) TR/FTIR spectroscopy method, (4) a sterility test, or (5) a bacterial identification test.

In one embodiment, the composition further comprises an alcohol. Non-limiting examples of alcohols that can be used include ethanol (e.g., about 20%) and benzyl alcohol (e.g., from about 1% to about 2%). In one specific embodiment, the composition consists essentially of about 8 M urea and about 20% ethanol.

In one embodiment, the invention provides a method for microbial bioburden reduction of a chromatography matrix, comprising contacting the chromatography matrix with a composition consisting essentially of about 4.0 M to about 12.0 M urea, wherein the contacting step results in one or more of a reduction in the amount of spore forming bacteria (e.g., *Bacillus pseudofirmus*) by at least 2 $\log_{10}$, a reduction in the amount of gram positive bacteria (e.g., *Microbacterium* spp.) by at least 5 $\log_{10}$, and a reduction in the amount of gram negative bacteria (e.g., *Stenotrophomonas maltophilia*) by at least 5 $\log_{10}$, in the chromatography matrix. In one specific embodiment, the contacting step results in a reduction in the amount of one or more of spore forming bacteria (e.g., *Bacillus pseudofirmus*), gram positive bacteria (e.g., *Microbacterium* spp.), and gram negative bacteria (e.g., *Stenotrophomonas maltophilia*), in the chromatography matrix, to below the limit of detection as determined by an assay, such as, for example, (1) a biofiltration assay, (2) microscopic bacterial staining, (3) IR/FTIR spectroscopy method, (4) a sterility test, or (5) a bacterial identification test.

In a further aspect, the invention provides a method for microbial bioburden reduction of a chromatography matrix, comprising contacting the chromatography matrix with a composition comprising from about 4.0 M to about 12.0 M guanidine hydrochloride, wherein the contacting step is performed for at least about 30 minutes. In one embodiment, the contacting step is performed for at least about 1 hour. In one embodiment, the composition comprises about 6 M guanidine hydrochloride.

In one embodiment, the composition further comprises an alcohol. Non-limiting examples of alcohols that can be used include ethanol (e.g., about 20%) and benzyl alcohol (e.g., from about 1% to about 2%). In one specific embodiment, the composition consists essentially of about 6 M guanidine hydrochloride and about 20% ethanol.

In one embodiment, the invention provides a method for microbial bioburden reduction of a chromatography matrix, comprising contacting the chromatography matrix with a composition consisting essentially of about 4.0 M to about 12.0 M guanidine hydrochloride, wherein the contacting step is performed for at least about 30 minutes. In one specific embodiment, the contacting step is performed for at least about 1 hour. In one specific embodiment, the composition consists essentially of about 6 M guanidine hydrochloride.

In a related aspect, the invention provides a method for microbial bioburden reduction of a chromatography matrix, comprising contacting the chromatography matrix with a composition comprising from about 4.0 M to about 12.0 M guanidine hydrochloride, wherein the contacting step results in one or more of a reduction in the amount of spore forming bacteria (e.g., *Bacillus pseudofirmus*) by at least 2 $\log_{10}$, a reduction in the amount of gram positive bacteria (e.g., *Microbacterium* spp.) by at least 4 $\log_{10}$, and a reduction in the amount of gram negative bacteria (e.g., *Stenotrophomonas maltophilia*) by at least 2 $\log_{10}$, in the chromatography matrix. In one specific embodiment, the contacting step results in a reduction in the amount of one or more of spore forming bacteria (e.g., *Bacillus pseudofirmus*), gram positive bacteria (e.g., *Microbacterium* spp.), and gram negative bacteria (e.g., *Stenotrophomonas maltophilia*), in the chromatography matrix, to below the limit of detection as determined by an assay, such as, for example, (1) a biofiltration assay, (2) microscopic bacterial staining, (3) IR/FTIR spectroscopy method, (4) a sterility test, or (5) a bacterial identification test.

In one embodiment, the composition further comprises an alcohol. Non-limiting examples of alcohols that can be used include ethanol (e.g., about 20%) and benzyl alcohol (e.g., from about 1% to about 2%). In one specific embodiment, the composition consists essentially of about 6 M guanidine hydrochloride and about 20% ethanol.

In one embodiment, the invention provides a method for microbial bioburden reduction of a chromatography matrix, comprising contacting the chromatography matrix with a composition consisting essentially of about 4.0 M to about 12.0 M guanidine hydrochloride, wherein the contacting step results in one or more of a reduction in the amount of spore forming bacteria (e.g., *Bacillus pseudofirmus*) by at least 2 $\log_{10}$, a reduction in the amount of gram positive bacteria (e.g., *Microbacterium* spp.) by at least 4 $\log_{10}$, and a reduction in the amount of gram negative bacteria (e.g., *Stenotrophomonas maltophilia*) by at least 2 $\log_{10}$, in the chromatography matrix. In one specific embodiment, the contacting step results in a reduction in the amount of one or more of spore forming bacteria (e.g., *Bacillus pseudofirmus*), gram positive bacteria (e.g., *Microbacterium* spp.), and gram negative bacteria (e.g., *Stenotrophomonas maltophilia*), in the chromatography matrix, to below the limit of detection as determined by an assay, such as, for example, (1) a biofiltration assay, (2) microscopic bacterial staining, (3) TR/FTIR spectroscopy method, (4) a sterility test, or (5) a bacterial identification test.

In one aspect, the invention provides a method for microbial bioburden reduction of a chromatography matrix, comprising contacting the chromatography matrix with a composition comprising from about 0.5 M to about 1.0 M acetic acid and (i) from about 4.0 M to about 12.0 M urea and/or (ii) from about 4.0 M to about 12.0 M guanidine hydrochloride, wherein the contacting step is performed for at least about 1 hour. In one specific embodiment, the composition further comprises an alcohol. Non-limiting examples of alcohols that can be used include ethanol (e.g., about 20%) and benzyl alcohol (e.g., from about 1% to about 2%).

In one embodiment of any of the above methods of the invention, the contacting step is conducted at a temperature between 15° C. and 30° C. In one specific embodiment, the contacting step is conducted at a temperature between 20° C. and 25° C.

In one embodiment of any of the above methods of the invention, the composition is substantially free of oxidants.

In one embodiment of any of the above methods of the invention, the composition does not comprise a peroxyacid.

In one embodiment of any of the above methods of the invention, the composition does not comprise a peroxide.

In one embodiment of any of the above methods of the invention, the composition does not comprise NaOH.

In one embodiment of any of the above methods of the invention, the contacting step is repeated at least once.

In one embodiment of any of the above methods of the invention, the chromatography matrix is packed in a chromatography column. In one specific embodiment, the chromatography column has an inner diameter between 0.5 cm and 1.5 cm and a bed height between 15 cm and 30 cm. In one specific embodiment, the chromatography column has an inner diameter of about 1 cm and a bed height of about 20 cm. In one specific embodiment, the chromatography column has an inner diameter between 40 cm and 1.6 meters and a bed height between 15 cm and 30 cm. In one specific embodiment, the chromatography column has an inner diameter of about 1.4 meters and a bed height of about 20 cm.

In one embodiment of any of the above methods of the invention, the chromatography matrix comprises a proteinaceous ligand coupled to a support. In one specific embodiment, the proteinaceous ligand comprises one or more immunoglobulin binding domains. In one specific embodiment, the proteinaceous ligand is Protein A or a fragment or a derivative thereof. In one specific embodiment, the proteinaceous ligand is selected from the group consisting of *Staphylococcus* Protein A, *Peptostreptococcus* Protein L, *Streptococcus* Protein G, *Streptococcus* Protein A, and fragments and derivatives thereof. In one specific embodiment, the chromatography matrix is selected from the group consisting of MabSelect™, MabSelect™ Xtra, MabSelect™ SuRe, MabSelect™ SuRe pcc, MabSelect™ SuRe LX, MabCapture™ A, nProtein A Sepharose 4 Fast Flow, Protein A Sepharose 4 Fast Flow, Protein A Mag Sepharose, Protein A Sepharose CL-4B, rmp Protein A Sepharose Fast Flow, rProtein A Sepharose 4 Fast Flow, Capto™ L, ProSep™-A, ProSep Ultra Plus, AbSolute™, CaptivA™ PriMab™, Protein A Diamond, Eshmuno™ A, Toyopearl™ AF-rProtein A, Amsphere™ Protein A, KanCapA™ Protein G Mag Sepharose Xtra, and Protein G Sepharose 4 Fast Flow. In one specific embodiment, the chromatography matrix is selected from the group consisting of MabSelect™ MabSelect™ Xtra, MabSelect™ SuRe, MabSelect™ SuRe PCC, and MabSelect™ SuRe LX. In one specific embodiment, the proteinaceous ligand is not measurably denatured after the method is performed.

In one embodiment, the invention provides a method for microbial bioburden reduction of MabSelect™ Xtra chromatography matrix, comprising contacting the chromatography matrix with a composition consisting essentially of about 0.5 M acetic acid, wherein the contacting step is performed for at least about 4 hours.

In another embodiment, the invention provides a method for microbial bioburden reduction of MabSelect™ Xtra chromatography matrix, comprising contacting the chromatography matrix with a composition consisting essentially of about 0.1 M acetic acid and about 20% ethanol, wherein the contacting step is performed for at least about 4 hours. In various embodiments, the contacting step is performed for at least about 1 hour, 1 to 5 hours, 1 to 10 hours, 1 to 25 hours, 1 to 200 hours, 1 to 375 hours, 1 to 400 hours, at least about 4 hours, 4 to 5 hours, 4 to 10 hours, 4 to 25 hours, 4 to 200 hours, 4 to 375 hours, or 4 to 400 hours.

In a further embodiment, the invention provides a method for microbial bioburden reduction of MabSelect™ Xtra chromatography matrix, comprising contacting the chromatography matrix with a composition consisting essentially of about 8 M urea, wherein the contacting step is performed for at least about 1 hour.

In yet another embodiment, the invention provides a method for microbial bioburden reduction of MabSelect™ Xtra chromatography matrix, comprising contacting the chromatography matrix with a composition consisting essentially of about 8 M urea and about 20% ethanol, wherein the contacting step is performed for at least about 1 hour.

In a further embodiment, the invention provides a method for microbial bioburden reduction of MabSelect™ Xtra chromatography matrix, comprising contacting the chromatography matrix with a composition consisting essentially of about 6 M guanidine hydrochloride, wherein the contacting step is performed for at least about 1 hour.

In another embodiment, the invention provides a method for microbial bioburden reduction of MabSelect™ Xtra chromatography matrix, comprising contacting the chromatography matrix with a composition consisting essentially of about 6 M guanidine hydrochloride and about 20% ethanol, wherein the contacting step is performed for at least about 1 hour.

In one embodiment, the invention provides a method for reducing microbial load before applying a composition comprising a pharmaceutical agent for purification comprising (a) providing a chromatography matrix; (b) performing any of the above methods of the invention; and (c) applying the composition comprising the pharmaceutical agent to the chromatography matrix.

It is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention is defined by the claims.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs.

The terms "about" and "approximately" are used interchangeably to mean within a statistically meaningful range of a value. Such a range can be within 50%, more preferably within 20%, still more preferably within 10%, and even more preferably within 5% of a given value or range.

As used herein, the terms "microbe" or "microorganism" encompass prokaryotic organisms including bacteria and archaea, and eukaryotic organisms, including fungi. These terms encompass both live cells and spores (for spore-forming organisms) as well as microbial products such as, e.g., endotoxins.

The terms "microbial bioburden reduction" and "microbe bioburden reduction" as used herein combines killing of microbes and some interference with the interaction between a microbe and a chromatography matrix. The reduction of microbial bioburden according to the present invention is not the same as any previously disclosed sanitization process that was designed to kill essentially all, or even at least 99%, of the microbes that might exist on a chromatography column or matrix.

Rather, the present invention includes methods capable of killing less than 80%, less than 70%, less than 60%, or 40-60% of non-spore forming microbes. In such an embodiment, less than 50%, less than 40%, less than 30%, less than 20% or less than 10%, or 10-20% of the spore forming microbes, such as *Bacillus*, on a column would be killed by the methods of the present invention.

Even though the present invention includes methods that do not kill all of the bacteria on a column, at least 85%, at least 90%, at least 95%, at least 97%, about 98%, about 99% or about 100% of the viable microbes capable of being detected by the biofiltration assay, or any other microbiological assay disclosed herein and known in the art are removed from the chromatography matrix after treatment. In some embodiments of the present invention, the level of microbial bioburden is reduced below GMP-acceptable levels in a pre-use flush sample, in an equilibration sample, in a load sample, or in all GMP samples from the load taken subsequently during that run. Even without killing all of the microbes, the present invention can reduce a microbial bioburden to below GMP alert levels because of interference between the interaction between a microbe and a chromatography matrix that also occurs during methods of the claimed invention. This interference may involve, but is not limited to mechanisms such as reducing the affinity, binding, or any other interaction between the microbe and the chromatography matrix. Such mechanisms are similar to the common strip step used on a chromatography column that impurities such as host cell proteins and DNA from a column. Accordingly, this interference could be detected after use of a method of the present invention, which does not kill all of the microbes, when the microbial bioburden has been reduced to levels consistent with the requirements of GMP production of a biologic pharmaceutical drug. By using one of the methods of the present invention that is not designed to kill all of the microbes on a column, the reagents are not necessarily as harsh and therefore are more favorable for approval from regulatory agencies, e.g., FDA or EMA, that have to approve the process and the product for market. Preferably, the same strip buffer components or at least the active agents that are used on a chromatography column during GMP production of a biologic pharmaceutical (acetic acid is common) can be used to reduce microbial bioburden when applied at a higher concentration (for example, 10×, 15×, or 20×) and for a longer contract time (for example, 3×, 4×, or 5×). Further, it may be more efficient for the same strip buffer to be used at a higher concentration for a longer time to reduce a microbial bioburden.

Any of the methods, aspects, and embodiments described herein can be used as part of a good manufacturing practice (GMP), or current good manufacturing practice (CGMP). Such practices must provide consistency in manufacturing steps and quality of product so as to meet requirements of regulatory bodies, such as the U.S. Food and Drug Administration. GMP and CGMP typically require a high degree of predictability and standardization in manufacturing processes, particularly with ensuring purity of the manufactured therapeutic biomolecules used in human patients. There are many failure points during a GMP or CGMP, in which a parameter is detected that requires stopping the process and/or scrapping the production batch. With the labor involved in growing cultures to produce biomolecules, great expense arises when a failure occurs.

If the bioburden or microbial load gets too high in a chromatography column, or matrix used in separation, various unpredictable and/or undesirable effects can arise. A failure point could be triggered so as to stop the process so that product contaminated with microbes is identified and not further produced. To prevent failure points, detection of a bioburden of at least 5 CFU per 10 mL can trigger an alert. A bioburden of at least 10 CFU per 10 mL can trigger action, which can include undertaking one or more of the methods or embodiments described herein, alone or in combination, to reduce the bioburden.

For example, microbes can be introduced into the product, rendering it unacceptable for therapeutic use. An excessive bioburden can also decrease column performance, which can interfere with purifying the product in a standardized and predictable way and possibly cause other failure points to be triggered. Therefore, it is desirable to use the herein described aspects and embodiments of reducing bioburden preemptively to ensure compliance with a GMP or CGMP, and to minimize failure point triggering, and the associated troubleshooting and downtime.

Any of the aspects or embodiments described herein may further comprise a step of applying a small molecule-containing or biomolecule-containing (e.g., monoclonal antibody-containing) preparation for purification after the contacting step. A method for reducing microbial load before applying a small molecule-containing or biomolecule-containing (e.g., monoclonal antibody-containing) preparation for purification can comprise the steps of any of the methods of microbe bioburden reduction described herein. Alternatively, a method for purifying a biomolecule can comprise conducting the steps of any methods described herein and then applying a preparation comprising the biomolecule to the chromatography matrix.

Any of the aspects or embodiments described herein may be performed after the chromatography matrix is removed from storage but before application of a drug-containing, biomolecule-containing, or monoclonal antibody-containing preparation for purification. During long term storage, a small amount of bacteria present in a chromatography matrix or column may grow and increase bioburden.

Any of the aspects or embodiments described herein may be used as part of an aseptic technique, or to support an aseptic technique. The resulting reduction in bioburden on the chromatography matrix can be sufficient for an aseptic technique, or can be used before or after other steps in an aseptic technique. The described methods of reducing bioburden can reduce the odds that an aseptic technique failure point would be triggered and can be used in response to an impending failure point trigger.

In another aspect, a MabSelect™ Xtra chromatography matrix undergoes microbe bioburden reduction by contacting the matrix with a composition consisting essentially of about 0.5 M acetic acid, for at least 4 hours. In various embodiments, the contacting step is performed for 4 to 5 hours, 4 to 10 hours, 4 to 25 hours, 4 to 200 hours, 4 to 375 hours, or 4 to 400 hours. In another aspect, a MabSelect™ Xtra chromatography matrix undergoes microbe bioburden reduction by contacting the matrix with a composition consisting essentially of 0.1 M acetic acid and about 20% ethanol, for at least 4 hours.

Various chromatography matrices may be used. The chromatography matrix may comprise a proteinaceous ligand coupled to a support. The proteinaceous ligand, in turn, may comprise one or more immunoglobulin binding domains. Other useful chromatography matrices include, without limitation, various ion exchange chromatography matrices, hydrophobic interaction chromatography (HIC) matrices, mixed mode chromatography matrices, and size exclusion chromatography matrices.

The proteinaceous ligand of the chromatography matrix may be Protein A or a fragment or a derivative thereof. Exemplary proteinaceous ligands include *Staphylococcus* Protein A, *Peptostreptococcus* Protein L, *Streptococcus* Protein G, *Streptococcus* Protein A, and fragments and derivatives of any of *Staphylococcus* protein A, *Peptostreptococcus* Protein L, *Streptococcus* Protein G, *Streptococcus* Protein A.

*Staphylococcus* Protein A may be found on the cell wall of the bacteria *Staphylococcus aureus*. Protein A may bind antibodies in the Fc region, between the CH2 and CH3 domains. Protein A may be cultured in *Staphylococcus aureus* or produced recombinantly in other bacteria, for example, *E. coli* or *Brevibacillus*. Fragments or derivatives of *Staphylococcus* Protein A may also bind to antibodies in the Fc region, between the CH2 and CH3 domains.

*Peptostreptococcus* Protein L may be found on the surface of *Peptostreptococcus* magnus and can bind to antibodies via an interaction with the antibody light chain. Unlike Protein A, Protein L may bind to single chain variable fragments (scFv) and Fab fragments. Fragments or derivatives of Protein L may also bind to the light chain of antibodies, single chain variable fragments (scFv) and Fab fragments.

*Streptococcus* Protein G may be found on the cell wall of group G Streptococcal strains. Protein G may bind antibodies in the Fab and Fc regions. Protein G may be produced recombinantly in other bacteria, for example, *E. coli*. Fragments or derivatives of Protein G may also bind to antibodies in the Fab and Fc regions.

The chromatography matrix may be a resin that is part of a column. One suitable resin is MabSelect SuRe™ from GE Healthcare. An exemplary column suitable for small scale purifications is packed with MabSelect SuRe™, is about 1.0 cm in diameter, and about 20 cm long. A larger column, such as 1.4 m×20 cm, can be used for manufacturing scale purifications.

More generally, the methods of the present invention can be used for chromatography columns of various sizes, including laboratory scale, large process scale, and very large process scale. In some embodiments, the chromatography column may have an inner diameter between 0.5 cm to 1.5 cm and a bed height of between 15 to 30 cm (e.g., 20 cm). The inner diameter may be between 0.7 to 1.2 cm, alternatively 0.9 to 1.4 cm, 1.2 to 1.5 cm, 1.0 to 1.2 cm, or about 1 cm. In some embodiments, the chromatography column may have an inner diameter of between 40 cm to 1.6 meters (e.g., 60 cm, 80 cm, 1.0 meter, 1.2 meters, or 1.4 meters). The chromatography column may have a bed height of between 15 to 30 cm (e.g., 20 cm).

Exemplary chromatography matrices include MabSelect™, MabSelect™ Xtra, MabSelect™ SuRe, MabSelect™ SuRe pcc, MabSelect™ SuRe LX, nProtein A Sepharose 4 Fast Flow, Protein A Sepharose 4 Fast Flow, Protein A Mag Sepharose, Protein A Sepharose CL-4B, rmp Protein A Sepharose Fast Flow, rProtein A Sepharose 4 Fast Flow, Capto™ L, ProSep™-A, ProSep Ultra Plus, AbSolute™ CaptivA™ PriMab™, Protein A Diamond, Eshmno™ A, Toyopearl™ AF-rProtein A, Amsphere™ Protein A, KanCapA™, Protein G Mag Sepharose Xtra, and Protein G Sepharose 4 Fast Flow.

MabSelect™, MabSelect™ Xtra, MabSelect™ SuRe, and MabSelect™ SuRe LX have a recombinant protein A ligand, produced in *E. coli*, that is attached to a highly cross-linked agarose matrix.

Microbe bioburden reduction can restore performance of a chromatography matrix so that it can be used for additional purification rather than being replaced. Thus, in any of the methods described herein, microbe bioburden reduction can be conducted after the chromatography matrix has been used. In such scenarios, bacteria and other microorganisms that may be introduced into the chromatography matrix from cell culture broths comprising a monoclonal antibody of interest, can be removed. Substantial expense can be saved when using chromatography matrices comprised of proteinaceous ligands, such as Protein A.

Furthermore, using acetic acid-containing solutions instead of commonly used sodium hydroxide-containing solutions can result in less denaturation of the protein ligand and less damage to the chromatography matrix. Denaturation of the protein ligand and/or damage to the chromatography matrix can be measured indirectly by assaying various performance characteristics of the chromatography matrix, e.g., by assaying the purity and abundance of the product that elutes from the matrix and by assaying residual elution of a component of the matrix (e.g., Protein A). For example, if the proteinaceous ligand is Protein A, the purity and abundance of monoclonal antibodies would be assayed. Exemplary assays include size exclusion chromatography (e.g., SE-HPLC and SE-UPLC), capillary electrophoresis (e.g., CE-SDS), capillary isoelectric focusing (iCIEF) that can optionally include whole column imaging. Also, residual Protein A from the column can be measured (e.g., by an assay comprising ELISA).

Microbe bioburden reduction undertaken according to the methods described herein can be a cost-effective way to maintain performance of a column comprising Protein A or other proteinaceous ligands, by removing bacteria without damaging the Protein A. For example, exposure of a Protein A-containing matrix to an acetic acid-comprising solution (e.g., 0.5 M acetic acid) for 375 or 400 hours does not lead to any statistically significant loss of performance of a column comprising Protein A. See, e.g., Example 6, Table 10 and FIGS. 5-19. For example, there is no statistically significant loss of purity of eluted monoclonal antibody by size exclusion chromatography, capillary electrophoresis under reducing or non-reducing conditions, or by capillary isoelectric focusing.

Microbe bioburden reduction according to the methods described herein can remove nearly all of the bacteria without killing all of the bacteria. Without wishing to be bound by theory, acetic acid can interfere with the affinity between bacteria and the proteinaceous ligand, e.g., protein A. A microbe-contaminated matrix or column can have microbes reduced according to methods described herein by disrupting interactions between microbial organisms and the resin. The bacteria would tend to remain in the acetic acid-containing solution. Removal of the bacteria may be further enhanced by repeating the contacting steps with acetic acid or undertaking additional flushing of the chromatography matrix with acetic acid-containing solutions.

In some embodiments, the method removes spore-forming bacteria from the chromatography matrix. Spore-forming bacteria have the ability to switch to endospore form. Endospore form is a stripped-down, dormant form to which the bacterium can reduce itself. Endospore formation is usually triggered by a lack of nutrients or harsh conditions, such as acidic or basic environment. Endospores enable bacteria to lie dormant for extended periods even in unfavorable conditions. When the environment becomes more favorable, the endospore can reactivate to the vegetative state. Examples of bacteria that can form endospores include *Bacillus* and *Clostridium*. These spore-forming bacteria are thought to be able to form endospore under normal operating conditions in chromatography purification processes due to the existence of unfavorable conditions for these spore-forming bacteria in the manufacturing process. There are many methods that can be used to detect spore-forming bacteria and those include but not limited to microscopic bacterial staining method, IR/FTIR spectroscopy method, sterility tests, and bacterial identification tests (e.g., biochemical reactions, 16S rRNA sequence determination, or taxa-specific sequence determinations).

In some embodiments, the method removes Gram positive bacteria from the chromatography matrix. In some embodiments, the method can remove Gram negative bacteria from the chromatography matrix. In some embodiments, the method removes spore-forming bacteria, Gram positive bacteria and Gram negative bacteria from the chromatography matrix. The contacting step may result in a reduction in the amount of one or more of spore forming bacteria, gram positive bacteria, and gram negative bacteria, in the chromatography matrix, to below the limit of detection of an assay selected from the group consisting of (1) a biofiltration assay, (2) microscopic bacterial staining, (3) IR/FTIR spectroscopy method, (4) a sterility test, and (5) a bacterial identification test (e.g., a biochemical reaction, 16S rRNA sequence determination, or a taxa-specific sequence determination). Biofiltration assays are described in the U.S. Pharmacopeia Chapter <71>, titled "Sterility Tests." In biofiltration assays, elutions from the column are passed through a filter that selectively binds bacteria. The filter is then plated on agar with appropriate media to grow bacteria, incubated, and the bacteria counted. Dilutions of the column elution can be performed as needed.

Microscopic bacteria staining is described in the U.S. Pharmacopeia Chapter <61>, titled "Microbial examination of nonsterile products: microbial enumeration tests". IR/FTIR spectroscopy methods are described in BRUKER Application Note AN #405 Current Research, Technology and Education Topics in Applied Microbiology Biotechnology A. Mendez-Vilas (Ed.) Microbiological tests are described in Reynolds, J. et al., "Differential staining of bacteria: endospore stain" Curr. Proc. Microbiol. 2009, Appendix3: Appendix 3J.

In some embodiments, the concentration of acetic acid in the composition is from about 0.1 M to about 1.0 M. In some embodiments, the concentration of acetic acid in the composition is from about 0.2 M to about 0.8 M. In some embodiments, the concentration of acetic acid in the composition is from about 0.4 M to about 0.7 M. In some embodiments, the concentration of acetic acid in the composition is about 0.5 M. In some embodiments, the concentration of acetic acid in the composition is from about 0.1 M to about 0.5 M. In some embodiments, the concentration of acetic acid in the composition is about 0.1 M.

In some embodiments, the concentration of urea in the composition is from about 4 M to about 12 M. In some embodiments, the concentration of urea in the composition is from about 6 M to about 10 M. In some embodiments, the concentration of urea in the composition is from about 6 M to about 8 M. In some embodiments, the concentration of urea in the composition is about 8 M.

In some embodiments, the concentration of guanidine hydrochloride in the composition is from about 3 M to about 10 M. In some embodiments, the concentration of guanidine hydrochloride in the composition is from about 4 M to about 8 M. In some embodiments, the concentration of guanidine hydrochloride in the composition is from about 5 M to about 7 M. In some embodiments, the concentration of guanidine hydrochloride in the composition is about 6 M.

In some embodiments, the concentration of guanidine hydrochloride in the composition is from about 3 M to about 10 M. In some embodiments, the concentration of guanidine hydrochloride in the composition is from about 4 M to about 8 M. In some embodiments, the concentration of guanidine hydrochloride in the composition is from about 5 M to about 7 M. In some embodiments, the concentration of guanidine hydrochloride in the composition is about 6 M.

In some embodiments, the pH of the solution is at least 2.0. The pH may be from 2.0 to 7.0. The pH may be from 2.5 to 6.5, from 3.0 to 6.0, from 4.0 to 7.0, from 2.0 to 5.0, from 3.5 to 5.5, from 3.0 to 4.0, or about 4.0. The pH may be about any of the following: 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0.

In some embodiments, the composition comprises ethanol. The composition may comprise 1-40% ethanol, 5-35% ethanol, 10-25% ethanol, 15-30% ethanol, 18-24% ethanol, about 20% ethanol, or 20% ethanol. In some embodiments, the composition comprises about 0.1M acetic acid and about 20% ethanol. In some embodiments, the composition consists essentially of about 0.1M acetic acid and about 20% ethanol. There are advantages to using ethanol, while and minimizing the amount of benzyl alcohol used, or avoiding benzyl alcohol due to toxicity in humans, or adverse effects in humans, that may arise from presence of benzyl alcohol.

In some embodiments, the composition further comprises an acetate salt. The acetate salt may serve as a buffer for compositions comprising acetic acid. For example, the composition may comprise sodium acetate in addition to acetic acid such that the composition is a buffer. The composition may comprise from 0.1 M sodium acetate to 1.0 M sodium acetate, 0.2 to 0.8 M sodium acetate, 0.4 to 0.7 M sodium acetate, about 0.5 M sodium acetate, or 0.5 M sodium acetate. Buffering the acetic acid with sodium acetate or another acetate salt may be effective to maintain the pH of the solution in the chromatography matrix. The pH may be at least 2.0, from about 2 to 3, from 2.0 to 3.0, from 2.0 to 7.0, from 2.5 to 6.5, from 3.0 to 6.0, from 4.0 to 7.0, from 2.0 to 5.0, from 3.5 to 5.5, from 3.0 to 4.0, or about 4.0. The pH may be about any of the following: 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0.

In some embodiments in which the composition comprises acetic acid, the contacting step is performed for at least one hour, alternatively for 1 to 4 hours, alternatively for at least 2 hours. In some embodiments, the contacting step is performed for 2 to 4 hours. In some embodiments, the contacting step is performed for at least 4 hours. In various embodiments, the contacting step is performed for 90 minutes to 6 hours, 2 hours to 5 hours, 4 hours to 5 hours, 4 hours to 6 hours, 90 minutes to 3 hours, 5 hours to 6 hours, 4 hours to 10 hours, 4 hours to 25 hours, 4 hours to 200 hours, 4 hours to 375 hours, or 4 hours to 400 hours.

In some embodiments in which the composition comprises urea, the contacting step is performed for at least 30 minutes, alternatively at least one hour, alternatively for at least two hours. In some embodiments, the contacting step is performed for one to two hours. In some embodiments, the contacting step is performed for at least two hours. In various embodiments, the contacting step is performed for 30 minutes to 4 hours, 1 hour to 3 hours, or 90 minutes to 2 hours.

In some embodiments in which the composition comprises guanidine hydrochloride, the contacting step is performed for at least 30 minutes, alternatively at least one hour, alternatively for at least two hours. In some embodiments, the contacting step is performed for one to two hours. In some embodiments, the contacting step is performed for at least two hours. In various embodiments, the contacting step is performed for 30 minutes to 4 hours, 1 hour to 3 hours, or 90 minutes to 2 hours.

In some embodiments in which the composition comprises urea or guanidine hydrochloride, the contacting step is performed for at least 30 minutes, alternatively for at least about 1 hour, alternatively for 1 to 4 hours, alternatively for at least 2 hours.

In some embodiments, the contacting step can be repeated. For example, the contacting step may be performed for about one hour and then repeated multiple times. In some embodiments, the contacting step is repeated 2, 3, 4, 5, or 6 times. By repeating the microbe bioburden reduction, the column may be exposed to additional acetic acid, which can result in additional disruption of bacteria and microorganisms from the chromatography matrix. Repeating the contacting step can lead to more flushing, or removal, of bacteria and microorganisms from the chromatography matrix, e.g., a Protein A ligand, and the column. The microbe bioburden reduction process may reduce bioburden more when conducted multiple times in succession.

The effectiveness of any of the microbe bioburden reduction methods described herein can be monitored by using any number of bioburden assays. One such assay is a filtration assay where a volume of eluate is passed through a filter membrane that traps the bacteria present in the eluate. The bacteria titer can be determined by placing the filter membrane on agar plates such that the bacteria on the filter membrane form colonies on the plates. The agar plates may contain trypticase soy agar (TSA). Culturing may occur for 3 to 7 days at temperatures between 25° C. and 37° C. The number of colonies is then counted. If there are too many colonies formed, dilutions of the eluate can be undertaken.

In some embodiments, there is a reduction in the amount of spore forming bacteria by at least 1.5 $\log_{10}$. For example, when a chromatography matrix is contaminated with *Bacillus pseudofirmus*, contacting such matrix with an 8 M urea solution, 8 M urea/20% ethanol solution, a 6 M guanidine hydrochloride solution, or a 6 M guanidine hydrochloride/20% ethanol solution, for at least one hour can reduce the number of *Bacillus pseudofirmus* by at least 1.5 $\log_{10}$.

In some embodiments, the binding capacity of the chromatography matrix is preserved over 10 or more cycles when the method for microbial bioburden reduction is undertaken. In other embodiments, the binding capacity is preserved over 50 or more cycles. In some other embodiments, the binding capacity is preserved over 100 or more cycles. In some embodiments, the binding capacity is preserved over 200 or more cycles.

In some embodiments, there is no substantial degradation of the chromatography matrix during the contacting step or over multiple contacting steps wherein the exposure to the composition is for at least 5 hours, at least 10 hours, at least 25 hours, at least 200 hours, at least 375 hours, or at least 400 hours. In some embodiments, there is no measurable degradation of the chromatography matrix during the contacting step or over multiple contacting steps wherein the exposure to the composition is for at least 5 hours, at least 10 hours, at least 25 hours, at least 200 hours, at least 375 hours, or at least 400 hours. In some embodiments, the degradation of the chromatography matrix is measured by the protein quality of a protein that binds to the matrix (e.g., a monoclonal antibody that binds to a Protein A matrix).

In some embodiments, the proteinaceous ligand is not measurably denatured. Denaturation can be determined using functional assays such as, e.g., measuring column performance, product yield and/or quality, leachable proteinaceous ligand from the matrix, denaturation of the proteinaceous ligand, etc.

In some embodiments, there is no measurable leaching of the proteinaceous ligand, or Protein A during the contacting step or over multiple contacting steps. In some embodiments, there is no statistically significant measurable leaching of the proteinaceous ligand, or Protein A after exposure of the chromatography matrix to the composition (e.g., 0.5 M acetic acid) for 5 hours, 10 hours, 25 hours, 200 hours, 375 hours or 400 hours. Measurement of leaching of Protein A is one such exemplary assay. Denaturation of Protein A can change its confirmation such that it no longer interacts with beads or other solid phase support in the chromatography matrix. The denatured Protein A then would leach off of the beads or solid support and enter the liquid phase. Detection of the proteinaceous ligand, or Protein A, in the eluate or liquid phase of the affinity column can thus indicate measurable denaturation. Denaturation of other proteinaceous ligands, besides Protein A, may also lead to their leaching from the chromatography matrix. In some embodiments, the measurement of leaching of Protein A and/or other proteinaceous ligands comprises ELISA. An exemplary assay is described in Example 6 and FIGS. 8, 13 and 18.

EXAMPLES

The following examples describe the various aspects and embodiments described above. However, the use of these and other examples anywhere in the specification is illustrative only and in no way limits the scope and meaning of any of the disclosure or of any exemplified term. Likewise, any claimed subject matter is not limited to any particular preferred embodiments described here. Indeed, many modifications and variations may be apparent to those skilled in the art upon reading this specification, and such variations can be made without departing in spirit or in scope from the aspects and embodiments disclosed herein. Any claimed subject matter is therefore to be limited only by the terms of the appended claims along with the full scope of equivalents to which those claims are entitled.

Example 1

Acetic Acid Solution Reduces Bioburden in a Protein A Column

Reduction of microbes in three packed 1 cm MabSelect™ Xtra columns was assessed by measuring the bioburden after the column is spiked with a particular bacterium and then again after reducing microbes with a 0.5 M acetic acid solution.

First, the column was flushed with two column volumes of water for injection (WFI). A 20 mL sample was collected and served as a negative control with respect to the amount of bacteria in the column.

In each of the three MabSelect™ Xtra columns, a representative microorganism was added to the column by adding the microorganism to WFI to form spiked WFI, wherein the microorganism is present in a titer of approximately 105 cfu/mL. One column was spiked with spore-forming bacteria, particularly *Bacillus psuedofirmus*. One column was spiked with Gram positive bacteria, particularly *Microbacterium* spp. The third column was spiked with Gram negative bacteria, particularly *Stenotrophomonas maltophilia.*

Each spiked WFI was then loaded onto each column. The columns were then flushed with 14 column volumes of WFI at 229 cm/hour, which were collected. Each column was held for one hour and then flushed again with the spiked WFI. A 20 mL sample was collected from each column as a positive control, with the amount of each of the Gram negative bacteria, Gram positive bacteria and spore-forming bacteria in the sample subsequently assayed.

Two column volumes of a microbe reducing solution of 0.5 M acetic acid were then applied to each column at 229 cm/hour. Each column was held for one hour and then flushed with two column volumes of WFI at 229 cm/hour. For *Microbacterium* spp. and *Stenotrophomonas maltophilia,* 1.5 column volumes of WFI were flushed through the column, then 1.5 column volumes of effluent were collected. For *Bacillus psuedofirmus,* 2 column volumes of an equilibration buffer (10 mM Sodium Phosphate, 500 mM Sodium Chloride, pH7.2) were flushed through the column, then 1.5 column volumes of effluent are collected.

The above experiment was repeated, with the columns held for four hours instead of one hour after the 0.5 M acetic acid microbe reducing solution was applied to the column.

A filtration-based bioburden assay was performed. Agar plates are prepared that have TSA media.

All of the above samples from the chromatography column were placed into a conical tube, inverted 10 times, and then passed through a filter manifold connected to sterile single use filter funnels having a 0.45 micron filter membrane, or a Milliflex® plus pump with a Milliflex® filter funnel unit having a 0.45 micron filter membrane. Sterile technique was used in handling the filter manifold or filter funnel unit so as not to introduce additional bacteria not found in the chromatography sample. Each membrane was then placed on top of the agar plate prepared with TSA media. The plates were incubated for 5-7 days at 30-35° C. The number of colony forming units was then counted and recorded.

Negative control plates are prepared by passing 100 mL of sterile PBS into a separate filter manifold or filter funnel unit with a 0.45 micron filter membrane. Each membrane is then placed on top of the agar plate prepared with TSA media. The plates were incubated for 5-7 days at 30-35° C. The number of colony forming units was then counted and expressed in a $\log_{10}$ format.

The tables below show the colony forming units pre-reduction and post-reduction for each of the three bacteria types.

TABLE 1

| Microbe Bioburden Reduction Solution | Microbe Bioburden Reduction Duration | *Bacillus pseudofirmus* Saturation/ Pre-Microbe Bioburden Reduction ($\log_{10}$) | *Bacillus pseudofirmus* Post-Microbe Bioburden Reduction ($\log_{10}$) |
|---|---|---|---|
| 0.5M acetic acid | 1 hour | 1.5 | 1.1 |
| 0.5M acetic acid | 4 hour | 3.4 | 0 |

TABLE 2

| Microbe Bioburden Reduction Solution | Microbe Bioburden Reduction Duration | *Microbacterium* spp. Saturation/ Pre-Microbe Bioburden Reduction ($\log_{10}$) | *Microbacterium* spp. Post-Microbe Bioburden Reduction ($\log_{10}$) |
|---|---|---|---|
| 0.5M acetic acid | 1 hour | 5.1 | 3.7 |
| 0.5M acetic acid | 4 hours | 5.6 | 0 |

TABLE 3

| Microbe Bioburden Reduction Solution | Microbe Bioburden Reduction Duration | *Stenotrophomonas maltophila* Saturation/ Pre-Microbe Bioburden Reduction ($\log_{10}$) | *Stenotrophomonas maltophila* Post-Microbe Bioburden Reduction ($\log_{10}$) |
|---|---|---|---|
| 0.5M acetic acid | 1 hour | 5.5 | 0 |
| 0.5M acetic acid | 4 hours | 6.2 | 0 |

For the *Bacillus pseudofirmus*, a 0.4 $\log_{10}$ reduction was observed when the 0.5 M acetic acid microbe bioburden reduction solution was held in the column for one hour. A 3.4 $\log_{10}$ reduction was observed when the 0.5 M acetic acid microbe bioburden reduction solution was held in the column for four hours.

For the *Microbacterium* spp. bacteria, a 1.4 $\log_{10}$ reduction was observed when the 0.5 M acetic acid microbe bioburden reduction solution was held in the column for one hour, and a 5.6 $\log_{10}$ reduction was observed when held for four hours.

For the *Stenotrophomonas maltophila* bacteria, a 5.5 $\log_{10}$ reduction was observed when the 0.5 M acetic acid microbe bioburden reduction solution was held in the column for one hour, and a 6.2 $\log_{10}$ reduction was observed when held for four hours.

0.5 M acetic acid is effective to remove a wide range of microorganisms, including spore-forming bacteria, when held in a protein A column for four hours.

Example 2

Acetic Acid/Ethanol Solution Reduces Bioburden in a Protein A Column

The steps in Example 1 above were undertaken, except that instead of 0.5 M acetic acid, a solution of 0.1 M acetic acid and 20% ethanol was used. As with Example 1, the 0.1 M acetic acid and 20% ethanol solution was held for one hour in one set of experiments and for four hours in another set of experiments. The results below also show a substantial decrease in the amount of bacteria after the microbe bioburden reduction solution was held in the column for either one or four hours.

TABLE 4

| Microbe Bioburden Reduction Solution | Microbe Bioburden Reduction Duration | *Bacillus pseudofirmus* Saturation/ Pre-Microbe Bioburden Reduction ($\log_{10}$) | *Bacillus pseudofirmus* Post-Microbe Bioburden Reduction ($\log_{10}$) |
|---|---|---|---|
| 0.1M acetic acid and 20% ethanol | 1 hour | 2.2 | 1.8 |
| 0.1M acetic acid and 20% ethanol | 4 hours | 2.5 | 0 |

TABLE 5

| Microbe Bioburden Reduction Solution | Microbe Bioburden Reduction Duration | *Microbacterium* spp. Saturation/ Pre-Microbe Bioburden Reduction ($\log_{10}$) | *Microbacterium* spp. Post-Microbe Bioburden Reduction ($\log_{10}$) |
|---|---|---|---|
| 0.1M acetic acid and 20% ethanol | 1 hour | 5.1 | 0.6 |
| 0.1M acetic acid and 20% ethanol | 4 hours | 5.1 | 0 |

TABLE 6

| Microbe Bioburden Reduction Solution | Microbe Bioburden Reduction Duration | *Stenotrophomonas maltophila* Saturation/ Pre-Microbe Bioburden Reduction ($\log_{10}$) | *Stenotrophomonas maltophila* Post-Microbe Bioburden Reduction ($\log_{10}$) |
|---|---|---|---|
| 0.1M acetic acid and 20% ethanol | 1 hour | 5.3 | 0 |
| 0.1M acetic acid and 20% ethanol | 4 hours | 5.1 | 0 |

For the *Bacillus pseudofirmus*, a 0.4 $\log_{10}$ reduction was observed when the 0.1 M acetic acid and 20% ethanol microbe bioburden reduction solution was held in the column for one hour. A 2.5 $\log_{10}$) reduction was observed when the 0.1 M acetic acid and 20% ethanol microbe bioburden reduction solution was held in the column for four hours.

For the *Microbacterium* spp. bacteria, a 4.5 $\log_{10}$ reduction was observed when the 0.1 Ni acetic acid and 20% ethanol microbe bioburden reduction solution was held in the column for one hour, and a 5.1 $\log_{10}$ reduction was observed when held for four hours.

For the *Stenotrophomonas maltophila* bacteria, a 5.3 $\log_{10}$ reduction was observed when the 0.1 M acetic acid and 20% ethanol microbe bioburden reduction solution was held in the column for one hour, and a 5.1 $\log_{10}$ reduction was observed when held for four hours.

Example 3

A Urea Solution Reduces Bioburden in a Protein A Column

The steps in Example 1 above were undertaken, except that instead of 0.5 M acetic acid, a solution of 8 M urea and a solution of 8 M urea/20% ethanol were used and only a one hour hold was measured. The results in Table 7 below show a substantial decrease in bacteria after the microbe bioburden reduction solution was held in the column for one hour. The reduction in spore-forming *B. psuedofirmus* was extensive and unexpected, particularly after only one hour of treatment.

TABLE 7

| Microbial Bioburden Reduction Solutions | Hold time | $\log_{10}$ of Reduction *Bacillus pseudofirmus* | *Microbacterium species* | *Stenotrophomonas maltophilia* |
|---|---|---|---|---|
| 8M Urea | 1 hr | 1.9 | 5.8 | 5.7 |
| 8M Urea/ 20% Ethanol | 1 hr | 1.6 | 5.7 | 6.7 |

Example 4

A Guanidine Hydrochloride Solution Reduces Bioburden in a Protein A Column

The steps in Example 1 above were undertaken, except that instead of 0.5 M acetic acid, a solution of 6 M guanidine hydrochloride and a solution of 6 M guanidine hydrochloride/20% ethanol were used and only a one hour hold was measured. The results in Table 8 below show a substantial decrease in bacteria after the microbe bioburden reduction solution was held in the column for one hour. The reduction in spore-forming *B. psuedofirmus* was extensive and unexpected, particularly after only one hour of treatment.

TABLE 8

| Microbial Bioburden | | Log$_{10}$ of Reduction | | |
|---|---|---|---|---|
| Reduction Solutions | Hold time | *Bacillus pseudofirmus* | *Microbacterium* species | *Stenotrophomonas maltophilia* |
| 6M Guanidine Hydrochloride | 1 hr | 1.6 | 5.4 | 2.4 |
| 6M Guanidine Hydrochloride/ 20% Ethanol | 1 hr | 2.0 | 4.7 | 4.7 |

Example 5

Tests of Microbial Bioburden Reduction Agents in Solution

A solution spike study was performed using 0.5 M acetic acid, where the extent of killing of *Bacillus psuedofirmus* and *Microbacterium* species was measured in solution, without chromatography matrix present. The data are illustrated in FIG. 1. There was little killing of *Bacillus psuedofirmus* observed after one hour, while there was some killing of *Microbacterium* species. These data illustrate that killing is not solely responsible for the microbial bioburden reduction of these bacteria, on a chromatography matrix, with 0.5 M acetic acid. Disruption of an interaction between the chromatography matrix and *Bacillus psuedofirmus* and *Microbacterium* species leads to increased reduction of bioburden than what would be expected from killing.

Figure 2:
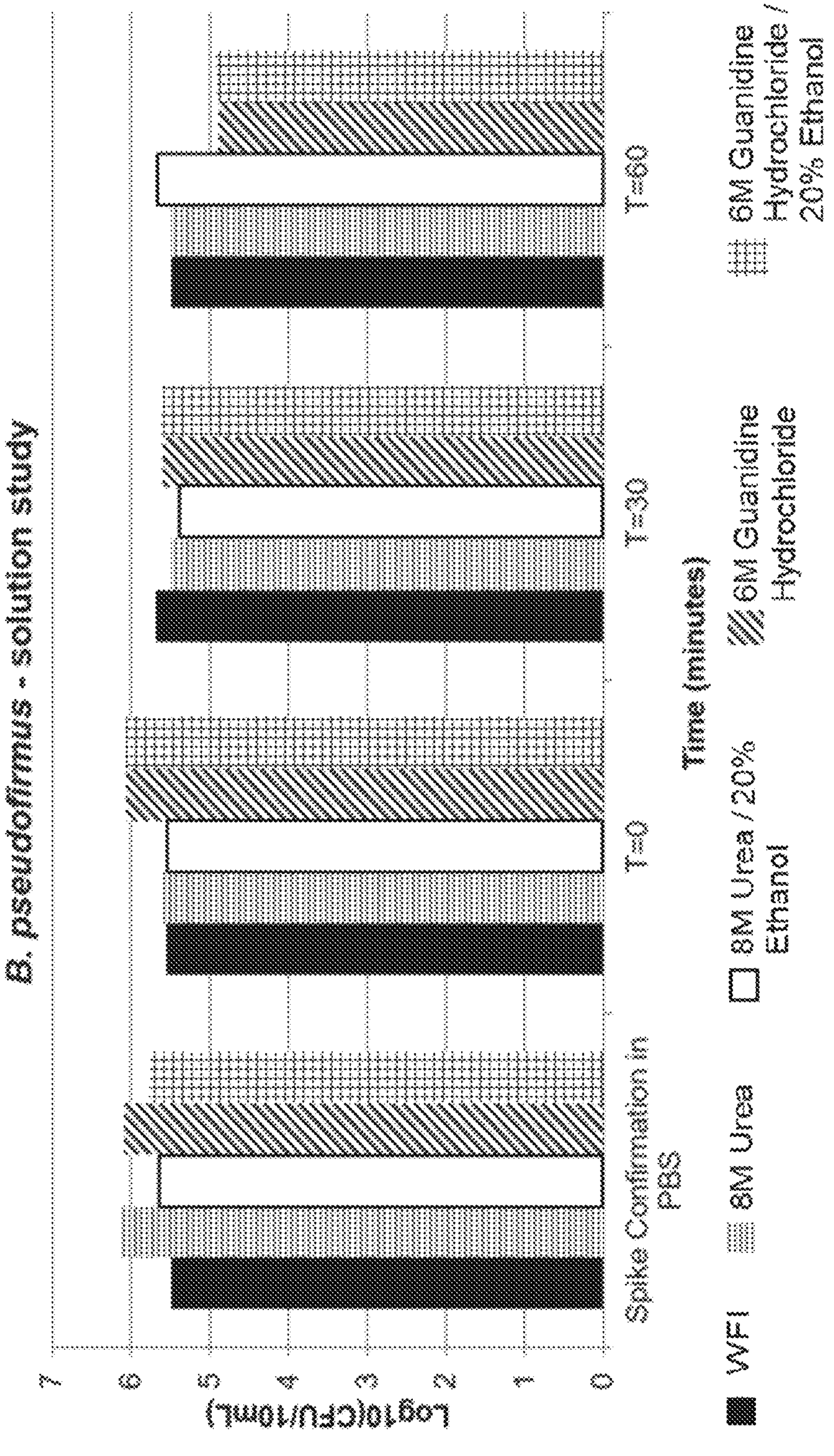
FIG. 2 illustrates the results of killing *Bacillus psuedofirmus* in solution, without chromatography matrix present, by spiking the solution with *Bacillus pseudofirmus* and measuring the bacterial titer. The following agents were added to separate solutions: (a) water for injection (WFI), (b) 8 M urea, (c) 8 M urea and 20% ethanol, (d) 6 M guanidine hydrochloride, (e) guanidine hydrochloride with 20% ethanol. A spike confirmation measurement in PBS was taken for each, as well as measurements at the 0 minute, 30 minute, and 60 minute time points. The black bar is for WFI, the horizontally striped bar is for 8 M urea, the white bar is for 8 M urea and 20% ethanol, the diagonally striped bar is for 6 M guanidine hydrochloride and the cross-hatched bar is for 6 M guanidine hydrochloride and 20% ethanol.
Figure 3:
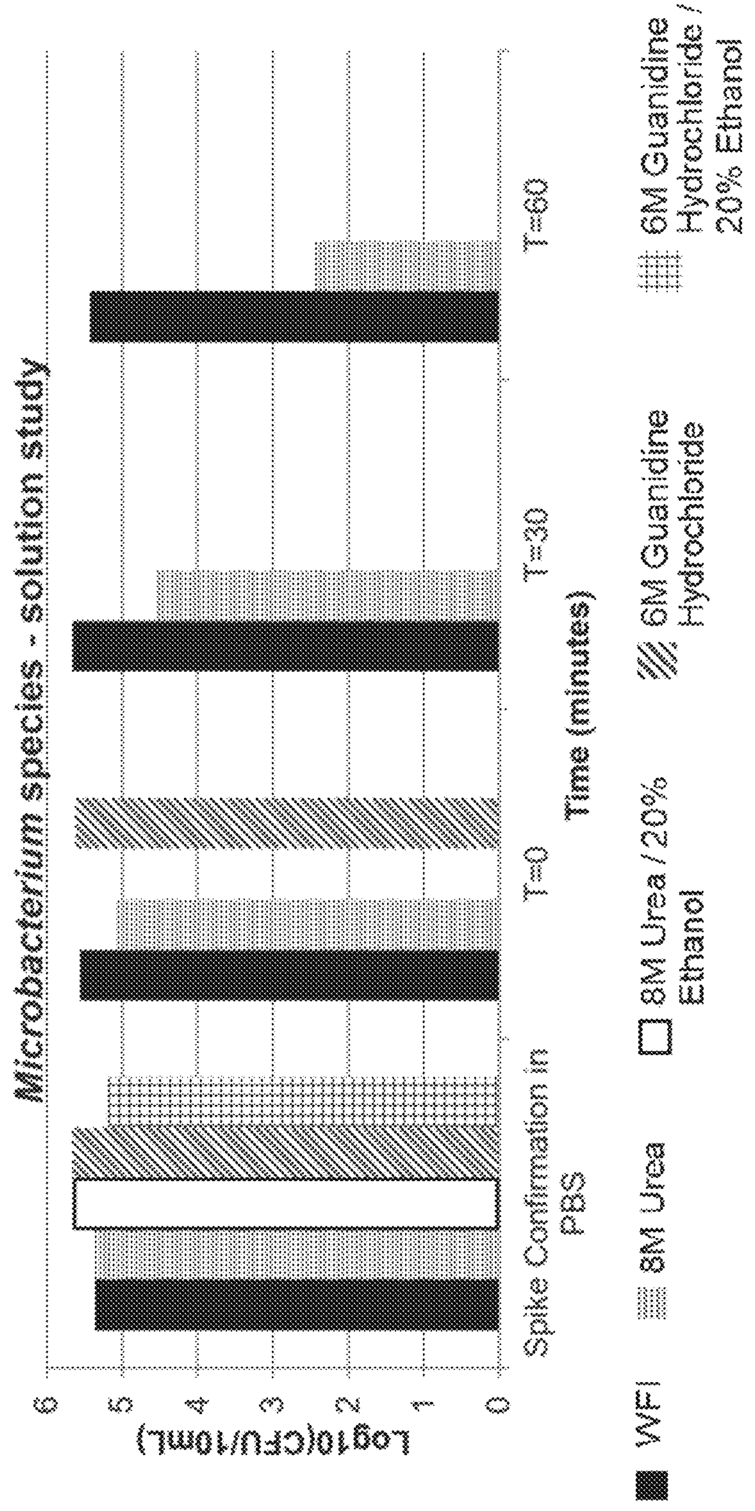
FIG. 3 illustrates the results of killing *Microbacterium* species in solution, without chromatography matrix present, by spiking the solution with *Bacillus pseudofirmus* and measuring the bacterial titer. The following agents were added: (a) water for injection (WFI), (b) 8 M urea, (c) 8 M urea and 20% ethanol, (d) 6 M guanidine hydrochloride, (e) guanidine hydrochloride with 20% ethanol. A spike confirmation measurement in PBS was taken, as well as measurements at the 0 minute, 30 minute, and 60 minute time points. The black bar is for WFI, the horizontally striped bar is for 8 M urea, the white bar is for 8 M urea and 20% ethanol, the diagonally striped bar is for 6 M guanidine hydrochloride and the cross-hatched bar is for 6 M guanidine hydrochloride and 20% ethanol.
Figure 4:
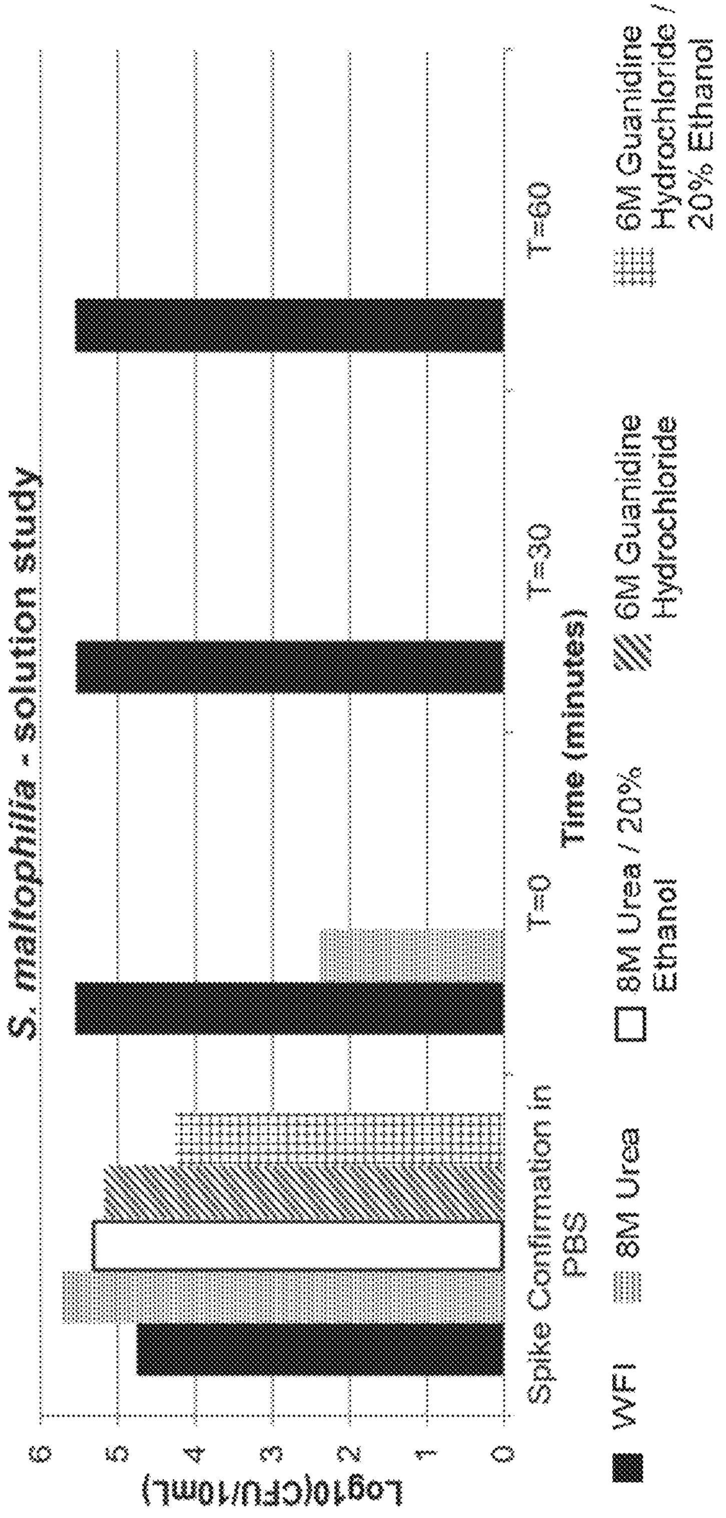
FIG. 4 illustrates the results of killing *Stenotrophomonas maltophilia* in solution, without chromatography matrix present, by spiking the solution with *Bacillus pseudofirmus* and measuring the bacterial titer. The following agents were added: (a) water for injection (WFI), (b) 8 M urea, (c) 8 M urea and 20% ethanol, (d) 6 M guanidine hydrochloride, (e) guanidine hydrochloride with 20% ethanol. A spike confirmation measurement in PBS was taken, as well as measurements at the 0 minute, 30 minute, and 60 minute time points. The black bar is for WFI, the horizontally striped bar is for 8 M urea, the white bar is for 8 M urea and 20% ethanol, the diagonally striped bar is for 6 M guanidine hydrochloride and the cross-hatched bar is for 6 M guanidine hydrochloride and 20% ethanol.
Figure 5:
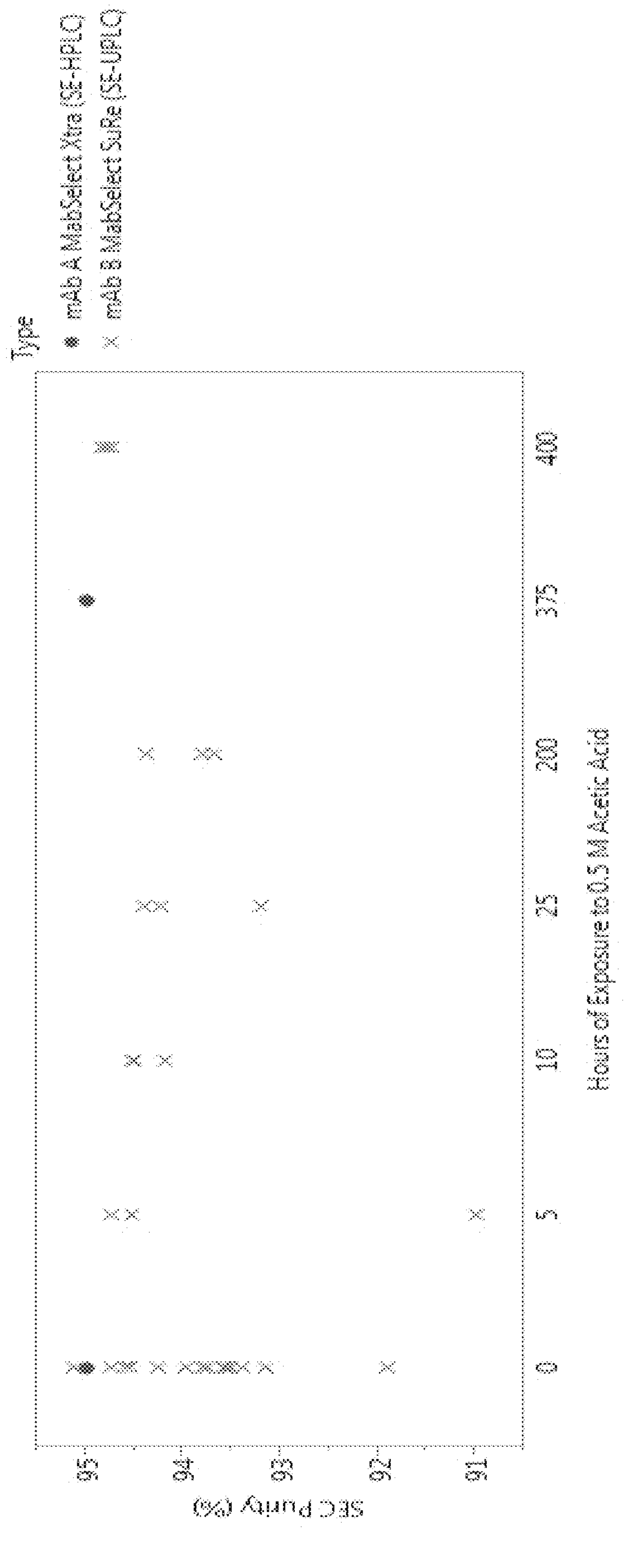
FIGS. 5-9 illustrate the results of various product quality studies performed on Protein A-containing resins (MabSelect™ Xtra and MabSelect™ SuRe) exposed to 0.5 M acetic acid for different lengths of time. The filled circles show the values for MabSelect™ Xtra that was exposed to 0.5 M acetic acid for 375 hours, or not exposed at all. The cross marks show the values for MabSelect™ SuRe that was not exposed to 0.5 M acetic acid for 5, 10, 25, 200 or 400 hours, or not exposed at all.
Figure 6:
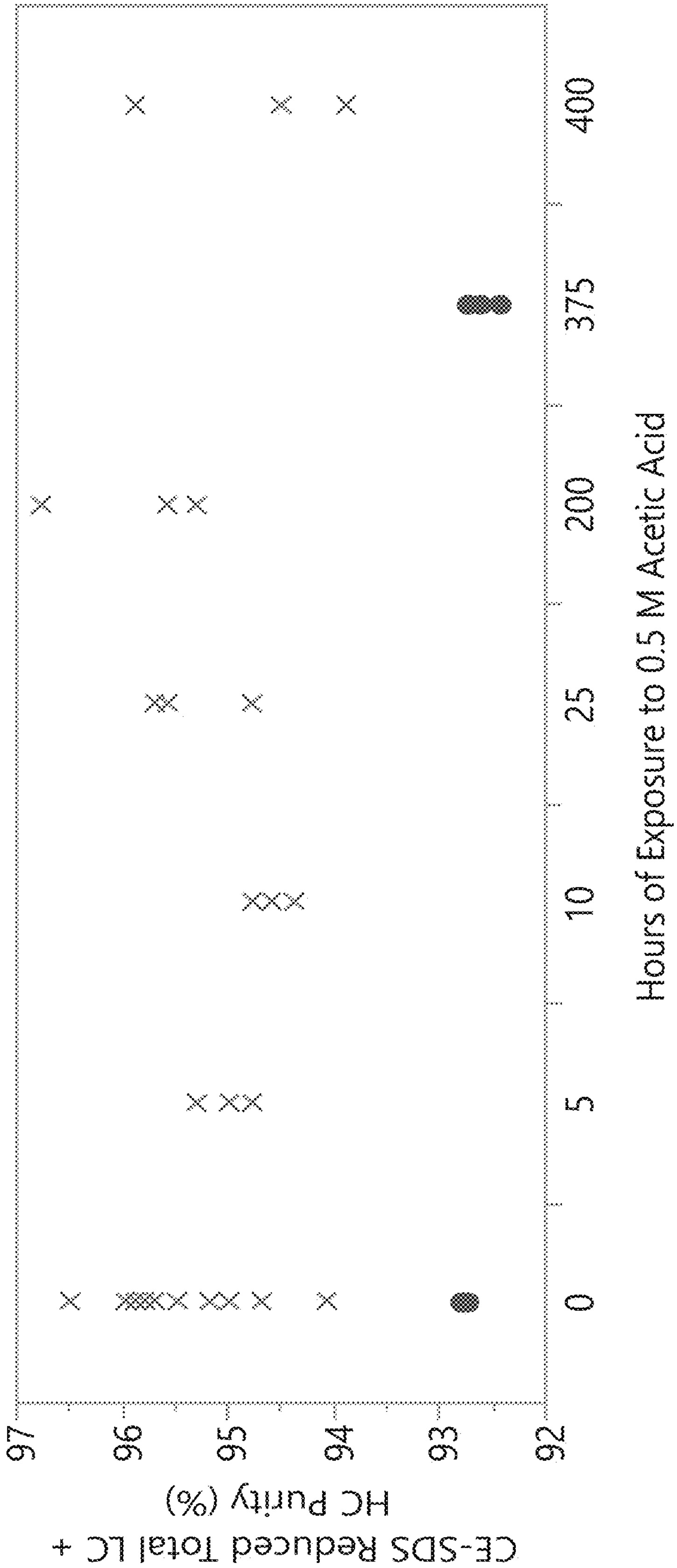
Figure 7:
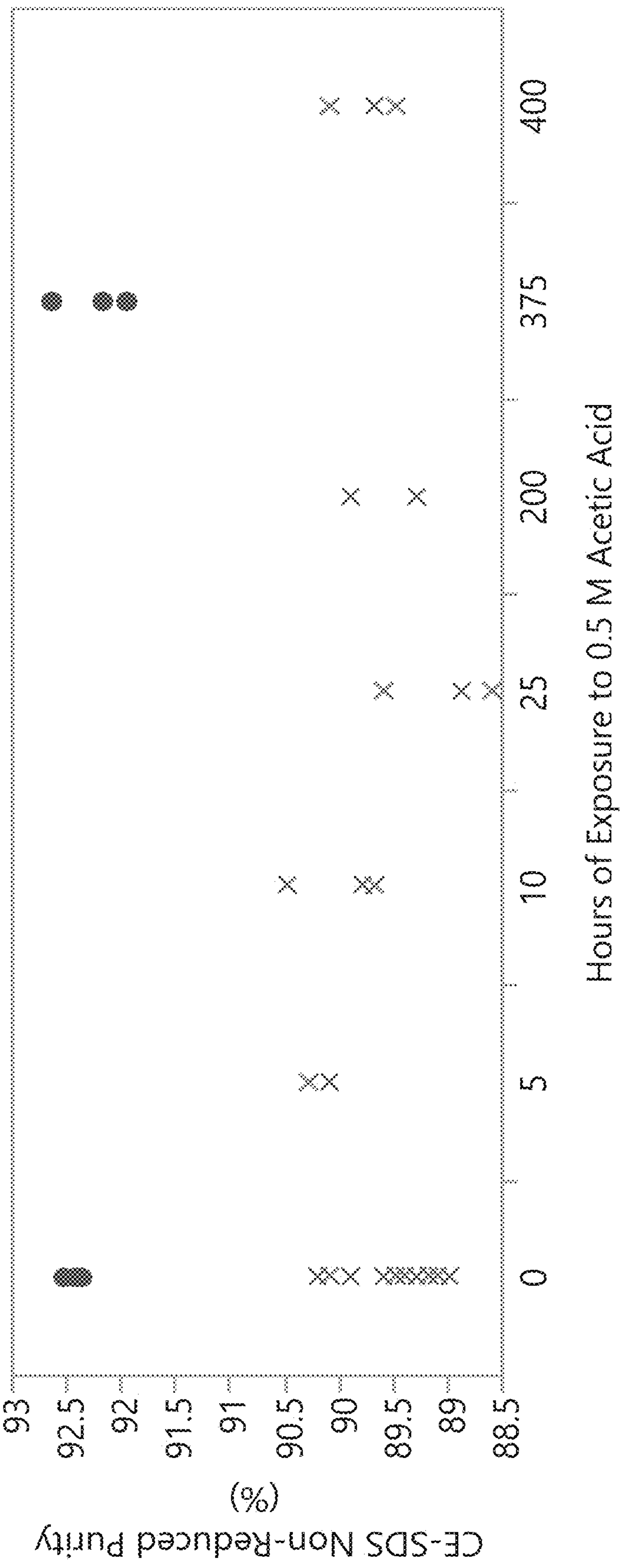
Figure 8:
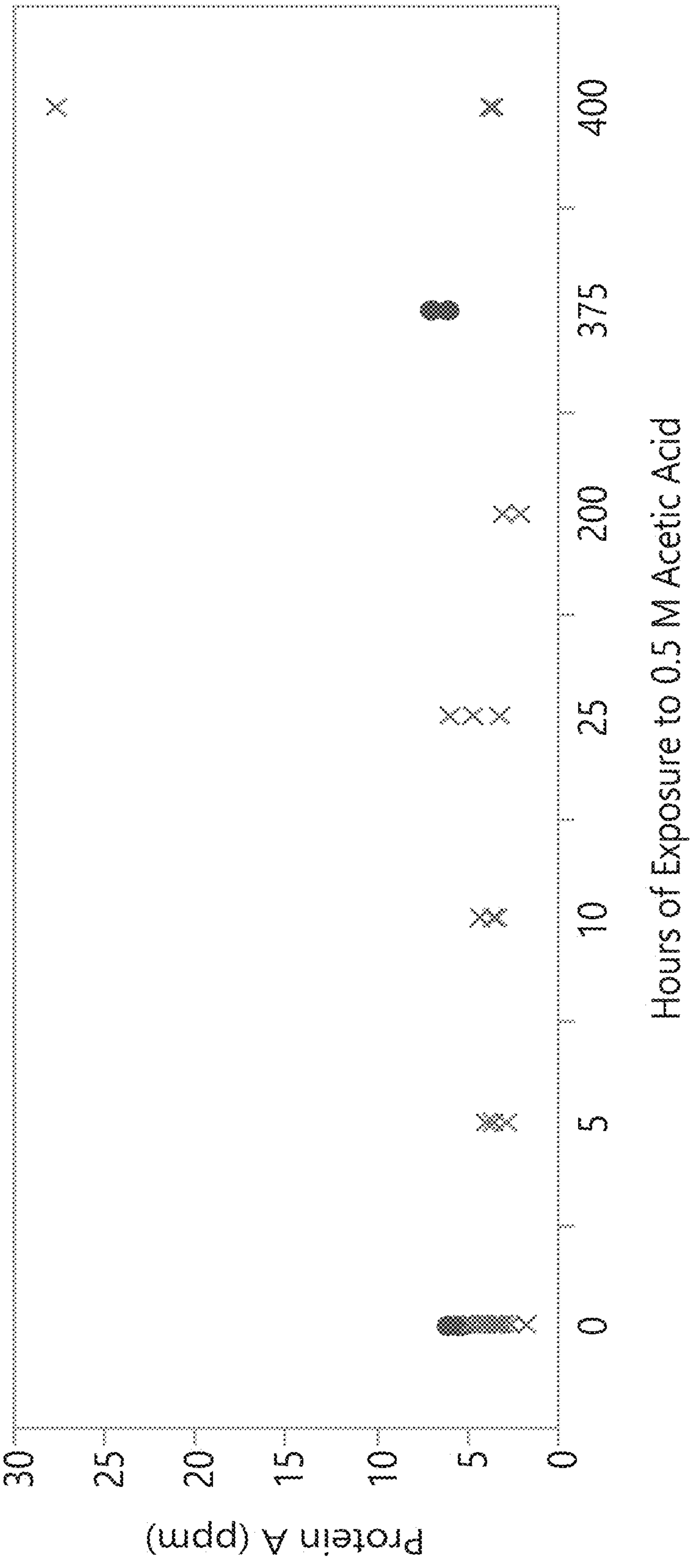
Figure 9:
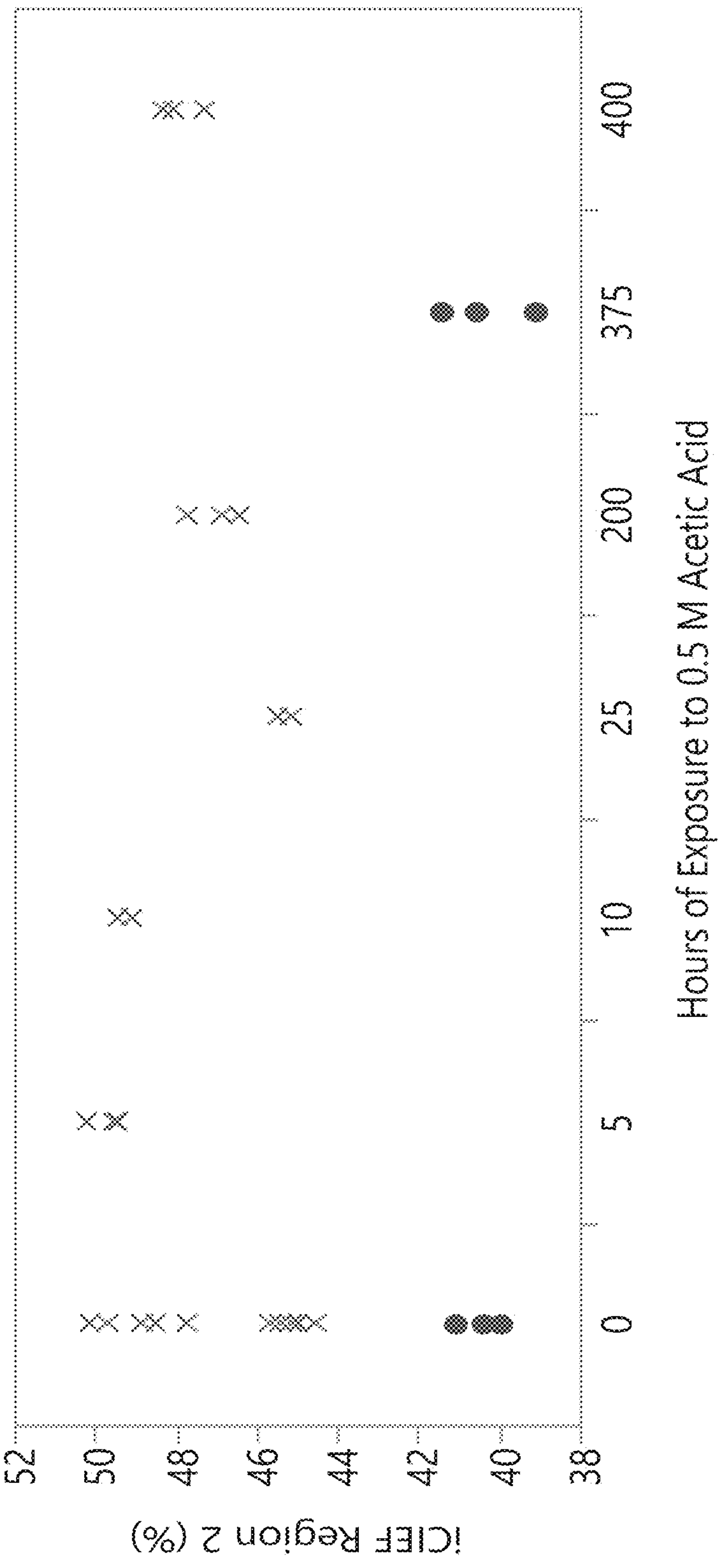
Figure 10:
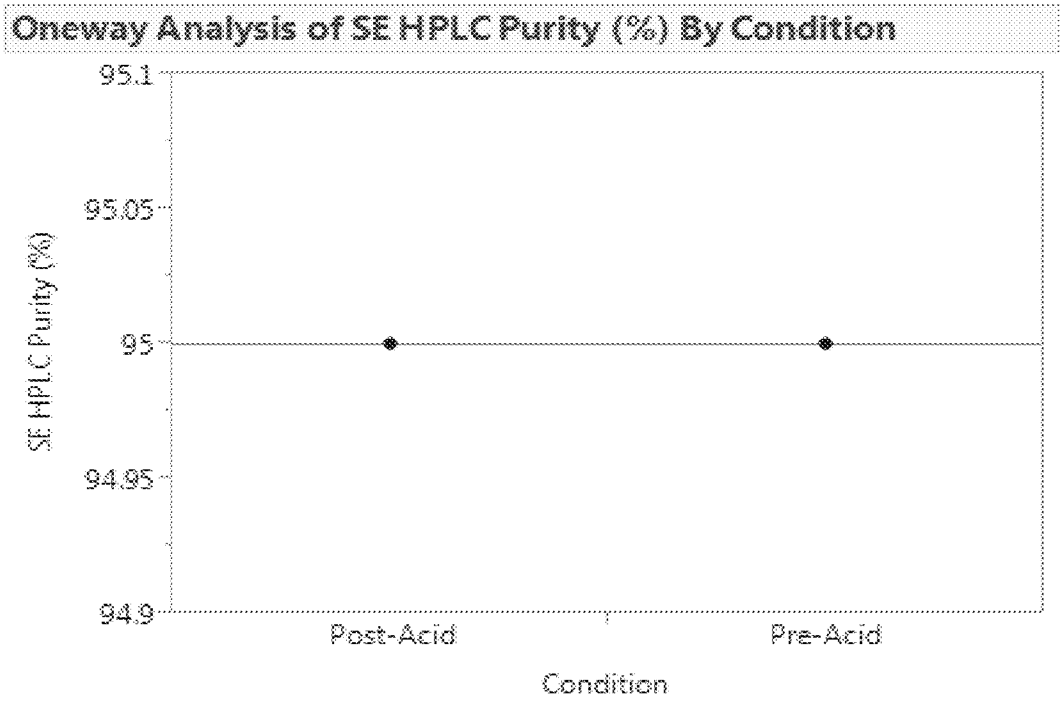
FIGS. 10-14 illustrate an ANOVA analysis of various product quality studies performed on the MabSelect™ Xtra Protein A resin. In the post-acid column, the filled circles reflect the values from Table 1 of 375 hours of exposure to 0.5 M acetic acid. In the pre-acid column, the filled circles reflect the values from Table 1 of zero hours of exposure to 0.5 M acetic acid. The diamond shapes indicate a range based on the 95% confidence intervals. All of the ranges for post-acid overlap with those of pre-acid. The ANOVA analysis shows no statistically significant negative effect on protein quality from prolonged exposure of the resin to 0.5 M acetic acid.
Figure 11:
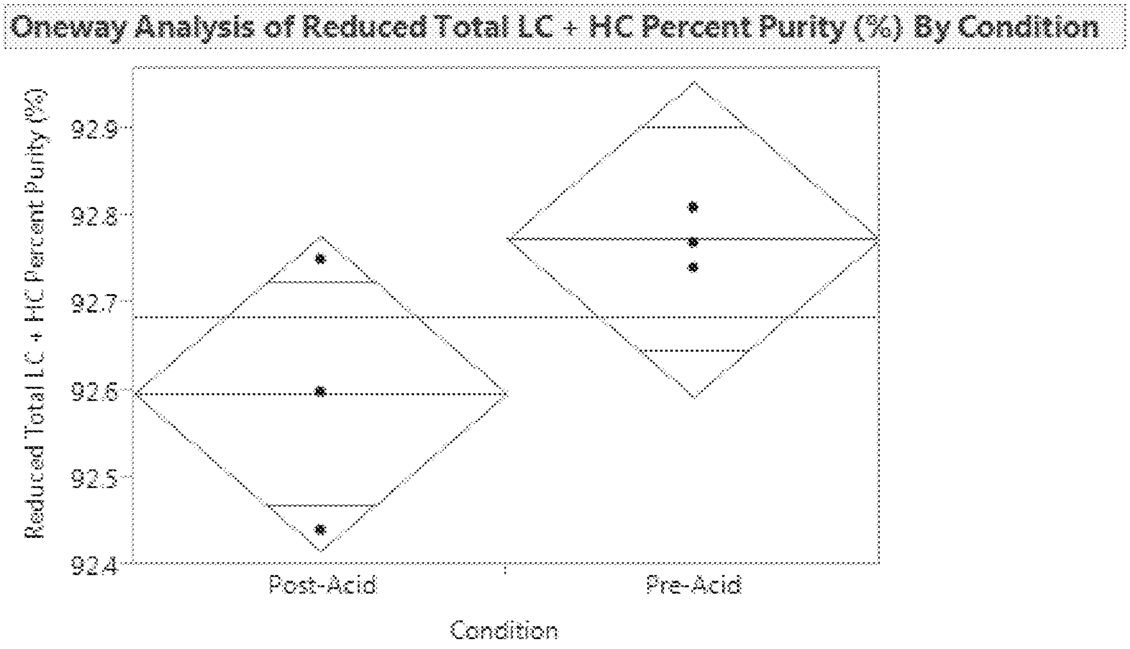
Figure 12:
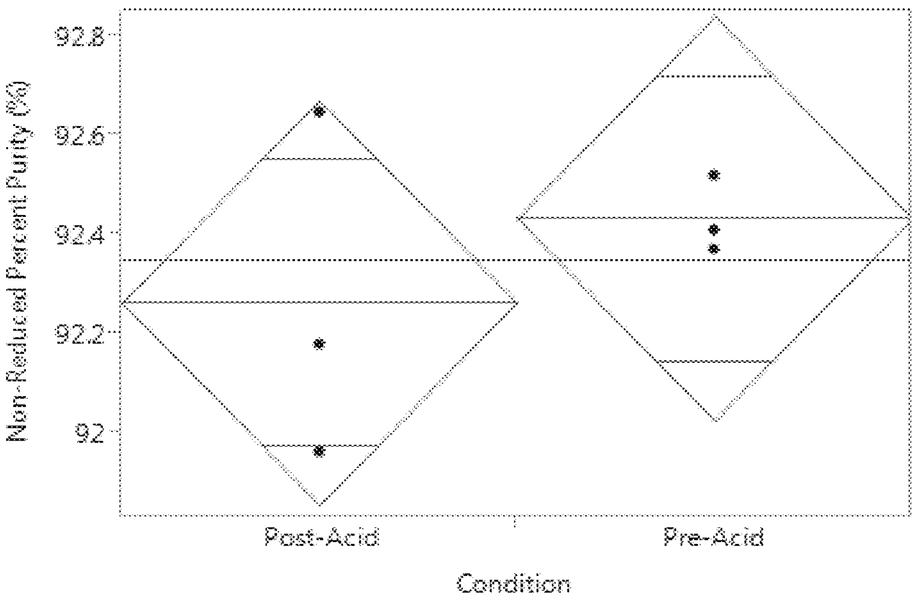
Figure 13:
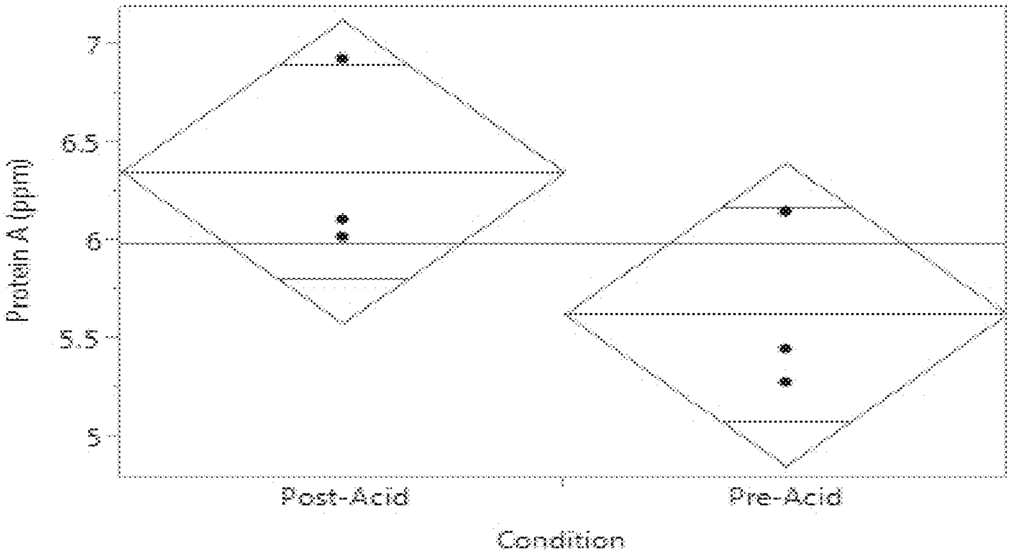
Figure 14:
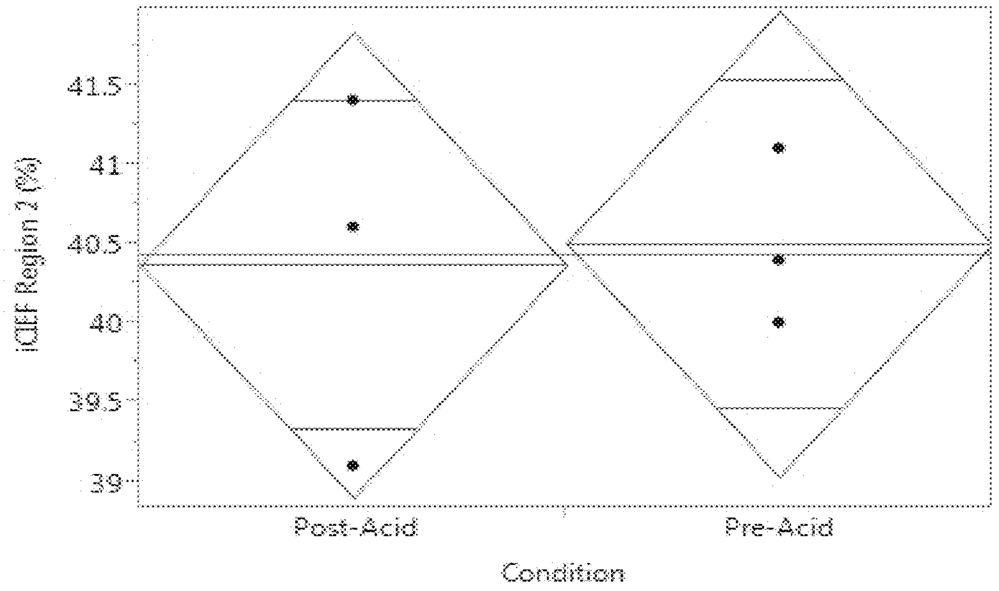
Figure 15:
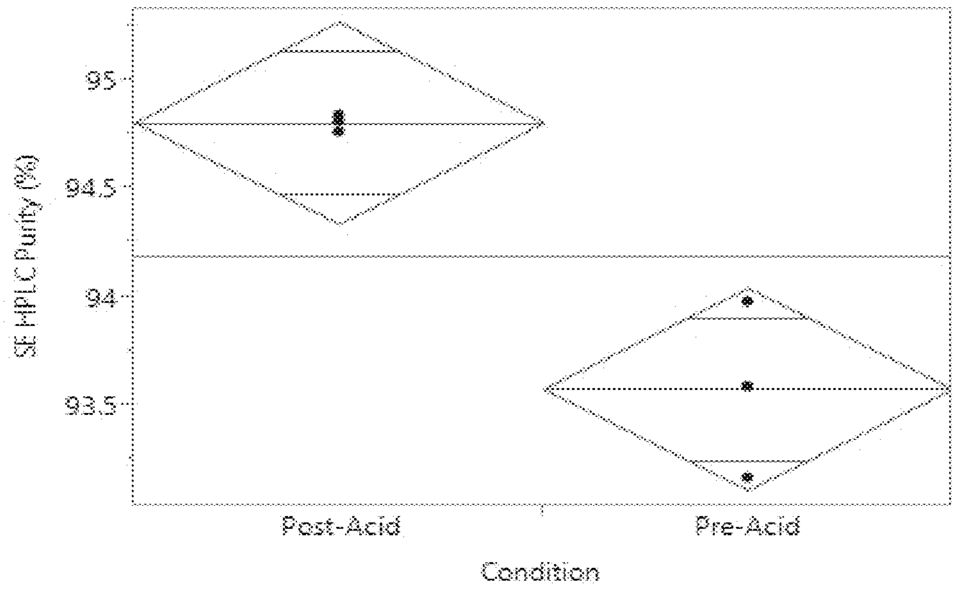
FIGS. 15-19 illustrate an ANOVA analysis of various product quality studies performed on the MabSelect™ SuRe Protein A resin. In the post-acid column, the filled circles reflect the values from Table 1 of 400 hours of exposure to 0.5 M acetic acid. In the pre-acid column, the filled circles reflect the values from Table 1 of zero hours of exposure to 0.5 M acetic acid. The diamond shapes indicate a range based on the 95% confidence intervals.
Figure 16:
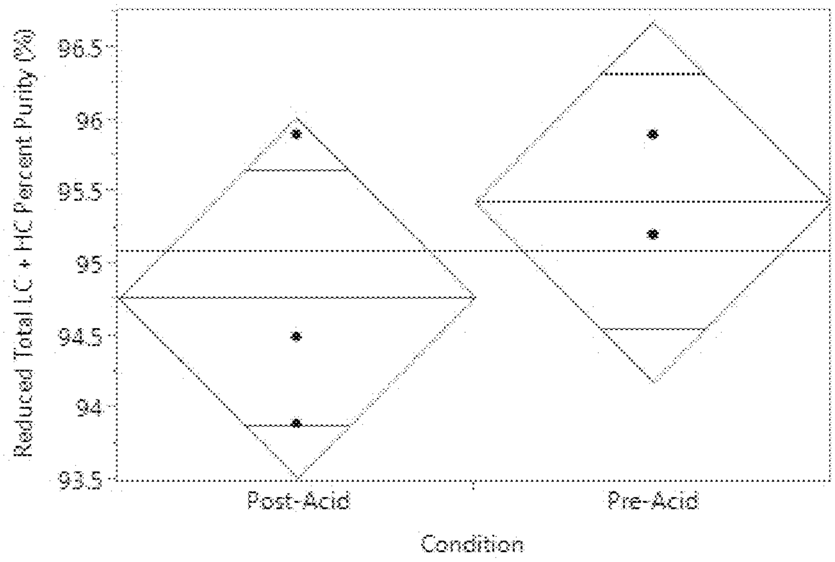
Figure 17:
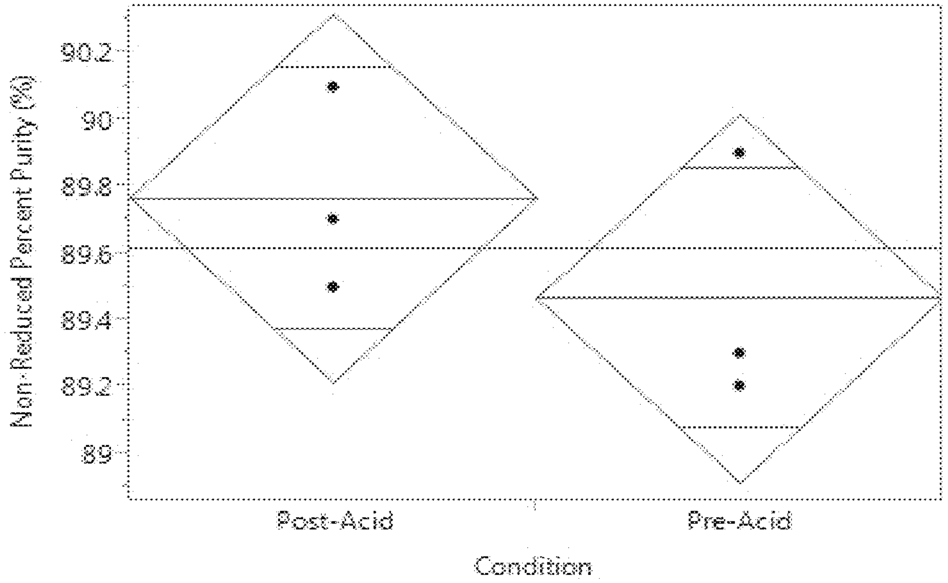
Figure 18:
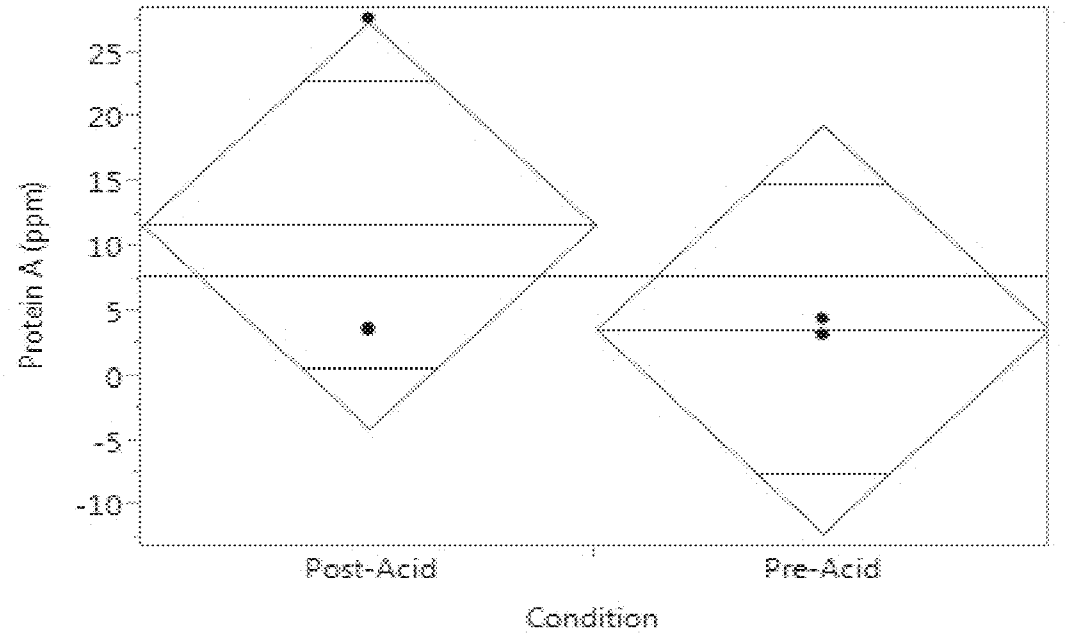
Figure 19:
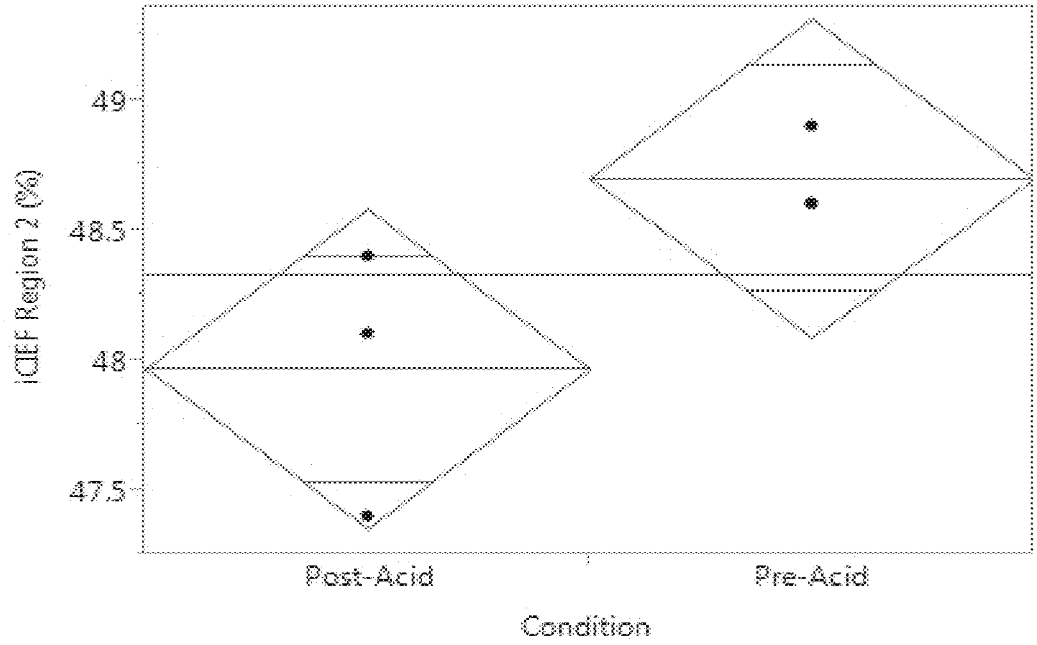

Additional solution spike studies were performed using other agents, where the extent of killing of *Bacillus psuedofirmus, Microbacterium* species, and *Stenotrophomonas maltophilia* were measured in solution. The following agents were added: (a) water for injection (WFI), (b) 8 M urea, (c) 8 M urea and 20% ethanol, (d) 6 M guanidine hydrochloride, (e) 6 M guanidine hydrochloride with 20% ethanol. A spike confirmation measurement in PBS was taken, as well as measurements at the 0 minute, 30 minute, and 60 minute time points. The data are shown in FIGS. 2-4, where the black bar is for WFI, the horizontally striped bar is for 8 M urea, the white bar is for 8 M urea and 20% ethanol, the diagonally striped bar is for 6 M guanidine hydrochloride and the cross-hatched bar is for 6 M guanidine hydrochloride and 20% ethanol.

For *Bacillus pseudofirmus*, the bioburden reduction is achieved by a combination of killing and disrupting of interactions between microbes and chromatography resin with at least the following solutions: 0.5 M acetic acid, 8 M urea and 8 M urea/20% ethanol, 6 M guanidine hydrochloride and 6 M guanidine hydrochloride/20% ethanol.

For *Microbacterium* species, bioburden reduction may occur by a combination of killing and disrupting interactions for 8 M urea and 0.5 M acetic acid, which are solutions that are not able to kill 100% of *Microbacterium* species. However, killing may be largely responsible for bioburden reduction with 8 M urea/20% ethanol, 6 M guanidine hydrochloride and 6 M guanidine hydrochloride/20% ethanol, which were observed to kill 100% of the *Microbacterium* in solution. Similarly for *Stenotrophomonas maltophilia,* 8 M urea, 8 M urea/20% ethanol were able to kill 100% *Stenotrophomonas maltophilia* in solution.

Examples 1-5 in summary show that 0.5 M acetic acid with a 4-hour hold, 8 M urea with a 1-hour hold and 8 M urea/20% ethanol with a 1-hour hold, 6 M guanidine hydrochloride with 1-hour hold and 6 M guanidine hydrochloride/20% ethanol with 1-hour hold were discovered to be an effective microbial bioburden reduction method for packed MabSelect™ Xtra column in manufacturing. As described in Examples 1-5, these agents are effective through the combination of killing the microbes and disrupting the interaction between microbial organisms and chromatography resin, or 100% to killing microbial organisms.

Additionally, MabSelect™ Xtra resin exposure to 0.5 M acetic acid resulted in minimal impact on Protein A resin.

Example 6

Affinity Columns Maintain Performance after Prolonged Exposure to Acetic Acid

The performance characteristics of two different chromatography affinity resins, MabSelect™ Xtra and MabSelect™ SuRe, were assessed after the resins were soaked in 0.5 M acetic acid for various lengths of time. Specifically, one fraction of MabSelect™ Xtra (used to capture mAb A) was soaked in 0.5 M acetic acid for 375 hours. As a negative control, another fraction of MabSelect™ Xtra was not soaked in 0.5 M acetic acid. Five different fractions of MabSelect™ SuRe (used to capture mAb B) were soaked in 0.5 M acetic acid for each of 5 hours, 10 hours, 25 hours, 200 hours, or 400 hours. As a control, another fraction of MabSelect™ SuRe was not soaked in 0.5 M acetic acid.

Five different experiments were then conducted on each of the above fractions above to assess performance. Size exclusion chromatography (SE-HPLC and SE-UPLC) was performed to assess mAb purity after purification on each of the above chromatography affinity resins.

TABLE 9

| Type of Column | Mobile Phase Buffer | Flow Rate (cm/hr) | Temperature (° C.) |
|---|---|---|---|
| MabSelect Xtra | 10 mM Sodium Phosphate, 500 mM Sodium Chloride | 229 | 20-25 |
| MabSelect SuRe | 10 mM Sodium Phosphate, 500 mM Sodium Chloride | 231 | 20-25 |

Two different capillary electrophoresis experiments were performed. CE-SDS was conducted for mAb A and PICO Microchip CE-Electrophoresis (PICO MCE-SDS) was conducted for mAb B. Capillary electrophoresis was conducted in SDS-containing gel-filled capillaries (CE-SDS) to measure the molecular weight distribution and relative abundance of light and heavy chain from monoclonal antibodies. These proteins were separated based on their size and electrophoretic mobility. The relative abundance of total light chain and heavy chain was conducted under reducing and non-reducing conditions. CE-SDS was performed using the IgG Purity Analysis Kit (Beckman Coulter, A10663) with a Bare Fused Silica Capillary (capillary length 57 cm, effective length 50 cm). PICO MCE-SDS was performed using Protein Express LabChip, LabChip® GXII, or LabChip® GXII Touch HT (Perkin Elmer, 760499 or 760528). Internal standards were used to calibrate the relative migration time.

To assay for effect of acetic acid on the Protein-A containing matrix, a residual protein A analysis was performed on eluates from the MabSelect™ Xtra and MabSelect™ SuRe columns by high throughput ELISA and quantified.

Capillary isoelectric focusing with whole-column imaging (iCIEF) was performed to quantify the amount of complementarity determining region 2 (CDR2) in a monoclonal antibody sample. Relative abundance of the CDR2 was calculated in each electropherogram by integrating the area under each of the sample-derived isoelectric point (pi) distribution peaks observed and calculating the percentage attributable to CDR2. The reported iCIEF Region 2 is the principal peak of neutral species and corresponds to the largest protein peak in the internal reference standard.

The results of each of the above analyses are shown in the following Table 10.

TABLE 10

| Resin | Hours of Exposure to 0.5M Acetic Acid | SE-UPLC Purity (%) | CE-SDS Reduced Total LC + HC Purity (%) | CE-SDS Non-Reduced Purity (%) | Protein A (ppm) | iCIEF Region 2 (%) |
|---|---|---|---|---|---|---|
| MabSelect | 0 | 95.00 | 92.77 | 92.41 | 6.15 | 40.40 |
| Xtra | | 95.00 | 92.74 | 92.37 | 5.28 | 40.00 |
| (used for | | 95.00 | 92.81 | 92.52 | 5.45 | 41.10 |
| capture | 375 | 95.00 | 92.75 | 92.65 | 6.11 | 41.40 |
| of mAb | | 95.00 | 92.44 | 92.18 | 6.93 | 40.60 |
| A) | | 95.00 | 92.60 | 91.96 | 6.02 | 39.10 |
| MabSelect | 0 | 94.27 | 95.50 | 89.00 | 3.50 | 45.20 |
| SuRe | | 94.62 | 94.70 | 90.10 | 4.50 | 50.20 |
| (used for | | 93.81 | 94.10 | 90.20 | 2.80 | 49.80 |
| capture | | 93.99 | 96.00 | 89.00 | 5.30 | 44.60 |
| of mAb | | 93.61 | 95.70 | 89.50 | 4.70 | 45.00 |
| B) | | 93.78 | 95.50 | 89.10 | 4.90 | 45.70 |
| | | 94.76 | 95.80 | 89.40 | 4.30 | 45.00 |
| | | 94.56 | 95.80 | 89.40 | 5.40 | 45.20 |
| | | 95.13 | 95.70 | 89.10 | 3.70 | 45.20 |
| | | 93.54 | 95.00 | 89.60 | 4.10 | 45.50 |
| | | 93.40 | 94.70 | 89.60 | 2.70 | 45.50 |
| | | 91.93 | 96.50 | 89.60 | 1.90 | 47.80 |
| | | 93.98 | 95.20 | 89.90 | 4.50 | 48.60 |
| | | 93.58 | 95.90 | 89.20 | 3.20 | 48.90 |
| | | 93.16 | 95.20 | 89.30 | 3.30 | 48.60 |
| | 5 | 94.76 | 95.30 | 90.30 | 3.70 | 49.60 |
| | | 91.01 | 95.00 | 90.10 | 4.10 | 50.30 |
| | | 94.54 | 94.80 | 90.30 | 2.90 | 49.50 |
| | 10 | 94.54 | 94.80 | 89.70 | 3.70 | 49.50 |
| | | 94.21 | 94.40 | 89.80 | 3.50 | 49.50 |
| | | 94.52 | 94.60 | 90.50 | 4.50 | 49.20 |
| | 25 | 93.22 | 94.80 | 88.60 | 3.40 | 45.60 |
| | | 94.24 | 95.70 | 88.90 | 4.70 | 45.20 |
| | | 94.41 | 95.60 | 89.60 | 6.10 | 45.60 |
| | 200 | 93.82 | 95.60 | 89.90 | 3.20 | 47.80 |
| | | 93.70 | 96.80 | 89.30 | 2.20 | 46.90 |
| | | 94.40 | 95.30 | 89.90 | 2.20 | 46.50 |
| | 400 | 94.84 | 95.90 | 89.50 | 3.80 | 47.40 |
| | | 94.76 | 94.50 | 90.10 | 27.70 | 48.40 |
| | | 94.81 | 93.90 | 89.70 | 3.60 | 48.10 |

The data from the above table are shown in each of FIGS. 5 through 9. Visual inspection of these figures shows no negative correlation between the performance characteristic and the length of time exposed to 0.5 M acetic acid.

Analysis of variance (ANOVA) for the product quality data was performed to assess for statistically significant differences between the resins before and after prolonged exposure to 0.5 M acetic acid using three chromatography runs per resin condition. FIGS. 10 through 14 show protein quality of the resultant mAb A pool after MabSelect Xtra purifications.

FIGS. 15 through 19 show protein quality of the resultant mAb B pool after MabSelect SuRe purifications. ANOVA analysis of protein quality shows no statistical significant ($p<0.05$) besides in the SE-UPLC percent purity of the mAb B MabSelect SuRe pool. However, the post-acid pool purity is higher than the pre-acid pool purity. Therefore, there is no negative effect on the mAb B pool after purification with MabSelect SuRe that has prolonged exposure to 0.5 M acetic acid.

The claimed subject matter is not to be limited in scope by the specific embodiments described herein. Indeed, various modifications of the claimed subject matter in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for microbial bioburden reduction of a chromatography matrix, comprising: contacting a chromatography matrix with a composition consisting essentially of about 0.1 M acetic acid and about 20% ethanol, wherein the contacting step is performed for about 1 hour to about 4 hours.

2. The method of claim 1, wherein the contacting step is capable of one or more of a reduction in the amount of spore forming bacteria by at least 3 $\log_{10}$, a reduction in the amount of gram positive bacteria by at least 5 $\log_{10}$, and a reduction in the amount of gram negative bacteria by at least 5 $\log_{10}$ in the chromatography matrix.

3. The method of claim 2, wherein the contacting step is capable of a reduction in the amount of one or more of spore forming bacteria, gram positive bacteria, and gram negative bacteria, in the chromatography matrix, to below the limit of detection as determined by an assay selected from the group consisting of (1) a biofiltration assay, (2) microscopic bacterial staining, (3) IR/FTIR spectroscopy method, (4) a sterility test, and (5) a bacterial identification test.

4. The method of claim 3, wherein the spore forming bacteria are *Bacillus pseudofirmus*, the gram positive bacteria are *Microbacterium* spp., and the gram negative bacteria are *Stenotrophomonas maltophilia.*

5. The method of claim 1, wherein the contacting step is performed for about 4 hours.

6. The method of claim 1, wherein the composition has pH between about 2 and about 3.

7. The method of claim 1, wherein the contacting step is conducted at a temperature between 15° C. and 30° C.

8. The method of claim 7, wherein the contacting step is conducted at a temperature between 20° C. and 25° C.

9. The method of claim 1, wherein said chromatography matrix comprises a proteinaceous ligand coupled to a support.

10. A method for microbial bioburden reduction of a chromatography matrix, comprising: contacting a chromatography matrix with a composition comprising about 0.1 M acetic acid and about 20% ethanol, wherein the contacting step is performed for about 1 hour to about 4 hours.

11. The method of claim 10, wherein the composition further comprises benzyl alcohol.

12. The method of claim 11, wherein the composition further comprises about 1% to about 2% benzyl alcohol.

13. The method of claim 10, wherein the composition further comprises an acetate salt.

14. The method of claim 10, wherein the contacting step is capable of one or more of a reduction in the amount of spore forming bacteria by at least 3 $\log_{10}$, a reduction in the amount of gram positive bacteria by at least 5 $\log_{10}$, and a reduction in the amount of gram negative bacteria by at least 5 $\log_{10}$ in the chromatography matrix.

15. The method of claim 10, wherein the contacting step is performed for about 4 hours.

16. The method of claim 10, wherein the contacting step is capable of a reduction in the amount of one or more of spore forming bacteria, gram positive bacteria, and gram negative bacteria, in the chromatography matrix, to below the limit of detection as determined by an assay selected from the group consisting of (1) a biofiltration assay, (2) microscopic bacterial staining, (3) IR/FTIR spectroscopy method, (4) a sterility test, and (5) a bacterial identification test.

17. The method of claim 16, wherein the spore forming bacteria are *Bacillus pseudofirmus*, the gram positive bacteria are *Microbacterium* spp., and the gram negative bacteria are *Stenotrophomonas maltophilia.*

18. The method of claim 10, wherein the composition has pH between about 2 and about 3, or wherein the contacting step is conducted at a temperature between 15° C. and 30° C.

19. The method of claim 18, wherein the contacting step is conducted at a temperature between 20° C. and 25° C.

20. The method of claim 10, wherein said chromatography matrix comprises a proteinaceous ligand coupled to a support.

* * * * *